United States Patent
Kagawa et al.

(10) Patent No.: US 11,608,493 B2
(45) Date of Patent: Mar. 21, 2023

(54) TRICHODERMA FILAMENTOUS FUNGUS MUTANT STRAIN AND METHOD OF PRODUCING PROTEIN

(71) Applicant: Toray Industries, Inc., Tokyo (JP)

(72) Inventors: Yusuke Kagawa, Kanagawa (JP); Shingo Hiramatsu, Kanagawa (JP); Katsushige Yamada, Kanagawa (JP)

(73) Assignee: Toray Industries, Inc., Tokyo (JP)

(*) Notice: Subject to any disclaimer, the term of this patent is extended or adjusted under 35 U.S.C. 154(b) by 78 days.

(21) Appl. No.: 17/059,821

(22) PCT Filed: May 30, 2019

(86) PCT No.: PCT/JP2019/021449
§ 371 (c)(1),
(2) Date: Nov. 30, 2020

(87) PCT Pub. No.: WO2019/230860
PCT Pub. Date: Dec. 5, 2019

(65) Prior Publication Data
US 2021/0214403 A1    Jul. 15, 2021

(30) Foreign Application Priority Data
May 31, 2018    (JP) .............................. JP2018-105256

(51) Int. Cl.
| | |
|---|---|
| *C12N 9/26* | (2006.01) |
| *C12P 21/04* | (2006.01) |
| *C12N 1/14* | (2006.01) |
| *C12N 9/42* | (2006.01) |
| *C12P 19/02* | (2006.01) |
| *C12P 19/14* | (2006.01) |
| *C12P 21/00* | (2006.01) |
| *C07K 14/37* | (2006.01) |

(52) U.S. Cl.
CPC ............ *C12N 9/2437* (2013.01); *C12P 19/02* (2013.01); *C12P 19/14* (2013.01); *C12P 21/00* (2013.01); *C12Y 302/01004* (2013.01); *C07K 14/37* (2013.01)

(58) Field of Classification Search
CPC ........ C12N 9/2437; C12N 19/14; C12P 21/00
See application file for complete search history.

(56) References Cited

U.S. PATENT DOCUMENTS

2019/0055614 A1    2/2019    Kobayashi et al.

FOREIGN PATENT DOCUMENTS

| | | |
|---|---|---|
| WO | 2014/202616 A2 | 12/2014 |
| WO | 2017/170918 A1 | 5/2017 |

OTHER PUBLICATIONS

ETR97140.1. GenBank Database. Mar. 2015.*
Studer. Residue mutations and their impact on protein structure and function: detecting beneficial and pathogenic changes. Biochem. J. (2013) 449, 581-594.*
Diego Martinez et al., "Genome sequencing and analysis of the biomass-degrading fungus Trichoderma reesei (syn. *Hypocrea jecorina*)," Nature Biotechnology, 2008, vol. 26, No. 5, pp. 553-560.
Juliano de Oliveira Porciuncula et al., "Single Nucleotide Polymorphism Analysis of a *Trichoderma reesei* Hyper-Cellulolytic Mutant Developed in Japan," Bioscience, Biotechnology, and Biochemistry, 2013, vol. 77, Issue 3, pp. 534-543.
Juliano de Oliveira Porciuncula et al., "Identification of Major Facilitator Transporters Involved in Cellulase Production during Lactose Culture of Trichoderma reesei PC-3-7," Bioscience, Biotechnology, and Biochemistry, 2013, vol. 77, Issue 5, pp. 1014-1022.
Weixin Zhang et al., "Two Major Facilitator Superfamily Sugar Transporters from *Trichoderma reesei* and Their Roles in Induction of Cellulase Biosynthesis," The Journal of Biological Chemistry, 2013, vol. 288, No. 46, pp. 32861-32872.
Database: GenBank [online], Accession No. EGR44419, Jul. 25, 2016 [retrieved on Jun. 13, 2019], Retrieved from the Internet: <URL:https://www.ncbi.nlm.nih.gov/protein/EGR44419.
Assen Marintchev et al., "eIF4G and CBP80 Share a Common Origin and Similar Domain Organization: Implications for the Structure and Function of eIF4G\," Biochemistry, 2005, vol. 44, No. 37, pp. 12265-12272 (Abstract).
Nicole LaRonde-LeBlanc, et al., "Structural Basis for Inhibition of Translation by the Tumor Suppressor Pdcd4," Molecular and Cellular Biology, Jan. 2007, vol. 27, No. 1, pp. 147-156.
Extended European Search Report dated Feb. 16, 2022, of counterpart European Patent Application No. 19812191.5.
R. Peterson et al., "Trichoderma reesei RUT-C30—Thirty Years of Strain Improvement," Microbiology, vol. 158, No. 1, pp. 58-68, Oct. 13, 2011, in English.
S. Le Crom et al., "Tracking the Roots of Cellulase Hyperproduction by the Fungus Trichoderma Reesei Using Massively Parallel DNA Sequencing," Proceedings of the National Academy of Sciences, vol. 106, No. 38, pp. 16151-16156, Sep. 22, 2009, in English.
M. Ike et al., "Cellulase Production on Glucose-Based Media by the UV-Irradiated Mutants of Trichoderma Reesei," Applied Microbiology and Biotechnology, Springer Berlin, De, vol. 87, No. 6, pp. 2059-2066, Jun. 12, 2010, in English.

* cited by examiner

*Primary Examiner* — Yong D Pak
(74) *Attorney, Agent, or Firm* — DLA Piper LLP (US)

(57) ABSTRACT

A mutant strain of a filamentous fungus of the genus *Trichoderma* having a reduced function of a polypeptide consisting of the amino acid sequence represented by SEQ ID NO: 2; and a method of producing a sugar from a cellulose-containing biomass, the method including: step a of producing a cellulase by cultivating a *Trichoderma reesei* mutant strain having a reduced function of a polypeptide consisting of the amino acid sequence represented by SEQ ID NO: 2, and step b of saccharifying the biomass by using the cellulase obtained in the step a.

5 Claims, No Drawings
Specification includes a Sequence Listing.

SEQUENCE LISTING

```
<160> NUMBER OF SEQ ID NOS: 14

<210> SEQ ID NO 1
<211> LENGTH: 1870
<212> TYPE: DNA
<213> ORGANISM: Trichoderma reesei

<400> SEQUENCE: 1
atgaccgtcc tcacctcacc tctggccagc tataatgtgg ccaacaagct gtacaaaacc      60
actctgctca acaccgtctg cctcgtggcc ggactgtcga tcttcttctt cggctatgat     120
cagggattga tgggcggtgt taacacgacg cgcgactatg ccgagcgcat gggctttggc     180
cactgggacg aagaccagaa cattgtcgtc gtcgataagc cgctgctgca gggcggtatc     240
gtagctgtct actatctccc cggaacgctg tgcggttgtc tgcttggcgg ttggcttggt     300
gatcgctatg gccgtatcaa aacaattgcc attgcctgtg cgtggagtgt ctgcgcagcc     360
gccctgcagg cctcagctat gaatgcgaac tggatgtttt gcggtatgtc gatgattctt     420
ggacaatcac aaccgaacta ttactgatga tgagatgaaa cagcccgcgt tctgaacggc     480
gtcggcactg gaatcttgaa cgcaatcacg cctgtgtggg caaccgagac tgctgctcac     540
acttctcgag gccagttcgt ttccattgag ttcaccctca acattcttgg tgttgttgta     600
gcctactggc tggaattgta cgtgcctcct cactcaggat ccccagtctt gtggaaagtc     660
tccctaatgc ggtggcagtg gtacttctaa atatcacgac aacacatcct ccttcatctg     720
gagattcccg gtcgccttcc agatcctccc cctaatcctt ctgttcctca tcatctggat     780
catgcctgaa tccccccgct ggctcgtcaa agtgggtcgt gaagaagagg ctcgcttcat     840
ccttggtcgt ctccgtggca atgagggcga ggacggcctc aaggcggaag cagagtacaa     900
tgatattgtc aacatccaca agcttgaagt agacaccgcc aagcagcaga gctacttctc     960
catgttcttt ggcattgggt ctggaaagct acacactggc cggcgcgtgc agctggtcat    1020
```

```
ctggctccag atattgcaag agtggatcgg tattgcggga atcaccattt acggccctga   1080
gatctttacg attgctggca tcagcgcaaa ggacagactc tgggttagcg ggatcaacaa   1140
tatcacatac atggtacgtt tagccaacac ctcctcacct caaagattcc atcacactaa   1200
cacgggagca gttcgccaca ctgatctgcg tcttcaccat cgatcgcata ggtcgccgtt   1260
ggactctgta ctggggagct gtcggccagg gcatttgcat gttcgtcgcc ggtggcctcg   1320
ctcgcgcaac catcaatgcc tcaggcaaag caagccagag ccacatcggc ggcgctgcaa   1380
cattctttgt gttcctctac actgccattt cggcgctac ctggctgacg gttccttggt    1440
tgtatccggc cgagattttc cctctgcagg ttagagccaa gggaaatgcc tggggtgtcg   1500
ttggctggtc cattggcaac ggctggtgtg taagtgcact tttcattctc ctctcccgtc   1560
tgggctcttc tggtctaatc ttctctaggt gctcctgctt cctacgatct tcaaggcgct   1620
caacgaaaag acactctaca ttttggcgc cgtcaacgcc ctgtccatcc tcgtcgtgtg     1680
ggctctgtac cccgaatcga atcaacgaac tctagaggag atggacctcg tctttgctag   1740
cgacagcatc tgggcctggg aggctgagcg taattttgcc aagctcaagg ctgaaaaccc   1800
ggatcttgtt cagggctcaa caaaccacgg agttgtagat attgagcaag ttgccgagcc   1860
aaaggagtag                                                          1870

<210> SEQ ID NO 2
<211> LENGTH: 543
<212> TYPE: PRT
<213> ORGANISM: Trichoderma reesei

<400> SEQUENCE: 2

Met Thr Val Leu Thr Ser Pro Leu Ala Ser Tyr Asn Val Ala Asn Lys
1               5                   10                  15

Leu Tyr Lys Thr Thr Leu Leu Asn Thr Val Cys Leu Val Ala Gly Leu
                20                  25                  30

Ser Ile Phe Phe Phe Gly Tyr Asp Gln Gly Leu Met Gly Gly Val Asn
            35                  40                  45

Thr Thr Arg Asp Tyr Ala Glu Arg Met Gly Phe Gly His Trp Asp Glu
        50                  55                  60

Asp Gln Asn Ile Val Val Asp Lys Pro Leu Leu Gln Gly Ile
65                  70                  75                  80

Val Ala Val Tyr Tyr Leu Pro Gly Thr Leu Cys Gly Cys Leu Leu Gly
                85                  90                  95

Gly Trp Leu Gly Asp Arg Tyr Gly Arg Ile Lys Thr Ile Ala Ile Ala
            100                 105                 110

Cys Ala Trp Ser Val Cys Ala Ala Leu Gln Ala Ser Ala Met Asn
            115                 120                 125

Ala Asn Trp Met Phe Cys Ala Arg Val Leu Asn Gly Val Gly Thr Gly
        130                 135                 140

Ile Leu Asn Ala Ile Thr Pro Val Trp Ala Thr Glu Thr Ala Ala His
145                 150                 155                 160

Thr Ser Arg Gly Gln Phe Val Ser Ile Glu Phe Thr Leu Asn Ile Leu
                165                 170                 175

Gly Val Val Val Ala Tyr Trp Leu Glu Phe Gly Thr Ser Lys Tyr His
            180                 185                 190

Asp Asn Thr Ser Ser Phe Ile Trp Arg Phe Pro Val Ala Phe Gln Ile
        195                 200                 205

Leu Pro Leu Ile Leu Leu Phe Leu Ile Ile Trp Ile Met Pro Glu Ser
```

```
          210                 215                 220
Pro Arg Trp Leu Val Lys Val Gly Arg Glu Glu Ala Arg Phe Ile
225                 230                 235                 240

Leu Gly Arg Leu Arg Gly Asn Glu Gly Glu Asp Gly Leu Lys Ala Glu
                245                 250                 255

Ala Glu Tyr Asn Asp Ile Val Asn Ile His Lys Leu Glu Val Asp Thr
            260                 265                 270

Ala Lys Gln Gln Ser Tyr Phe Ser Met Phe Gly Ile Gly Ser Gly
        275                 280                 285

Lys Leu His Thr Gly Arg Arg Val Gln Leu Val Ile Trp Leu Gln Ile
    290                 295                 300

Leu Gln Glu Trp Ile Gly Ile Ala Gly Ile Thr Ile Tyr Gly Pro Glu
305                 310                 315                 320

Ile Phe Thr Ile Ala Gly Ile Ser Ala Lys Asp Arg Leu Trp Val Ser
                325                 330                 335

Gly Ile Asn Asn Ile Thr Tyr Met Phe Ala Thr Leu Ile Cys Val Phe
            340                 345                 350

Thr Ile Asp Arg Ile Gly Arg Arg Trp Thr Leu Tyr Trp Gly Ala Val
        355                 360                 365

Gly Gln Gly Ile Cys Met Phe Val Ala Gly Leu Ala Arg Ala Thr
    370                 375                 380

Ile Asn Ala Ser Gly Lys Ala Ser Gln Ser His Ile Gly Gly Ala Ala
385                 390                 395                 400

Thr Phe Phe Val Phe Leu Tyr Thr Ala Ile Phe Gly Ala Thr Trp Leu
                405                 410                 415

Thr Val Pro Trp Leu Tyr Pro Ala Glu Ile Phe Pro Leu Gln Val Arg
            420                 425                 430

Ala Lys Gly Asn Ala Trp Gly Val Val Gly Trp Ser Ile Gly Asn Gly
        435                 440                 445

Trp Cys Val Leu Leu Pro Thr Ile Phe Lys Ala Leu Asn Glu Lys
    450                 455                 460

Thr Leu Tyr Ile Phe Gly Ala Val Asn Ala Leu Ser Ile Leu Val Val
465                 470                 475                 480

Trp Ala Leu Tyr Pro Glu Ser Asn Gln Arg Thr Leu Glu Glu Met Asp
                485                 490                 495

Leu Val Phe Ala Ser Asp Ser Ile Trp Ala Trp Glu Ala Glu Arg Asn
            500                 505                 510

Phe Ala Lys Leu Lys Ala Glu Asn Pro Asp Leu Val Gln Gly Ser Thr
        515                 520                 525

Asn His Gly Val Val Asp Ile Glu Gln Val Ala Glu Pro Lys Glu
    530                 535                 540
```

<210> SEQ ID NO 3
<211> LENGTH: 7115
<212> TYPE: DNA
<213> ORGANISM: Artificial Sequence
<220> FEATURE:
<223> OTHER INFORMATION: DNA fragment for transformation.

<400> SEQUENCE: 3

```
cttaaggacc ggtggtgatg gcttagagct ccaccgactc gtcccagttc ttgactcagg    60
cccacggaca tcattggtgc gcataataac cgacaaaagc cggagcgatc gacagacgtg   120
ccgatgcgc gcgttgctgg gctgtcaacg ctccctgagg gctgtaacag agtgacgaca   180
agaacagtat tccgggcata ctagtatcag ccagctccag cttttcccca tggagaaccc   240
```

```
caaactggag gcttctcttg cgataccatc tcatcattgg acagcgaccg gatggctccg     300
acgaagcgtt taagcgtctc agctggcgaa tgggatcccc tcattctgaa cagggagccc     360
gttttaggat accatttcct tcggaaacga tgagctttt gatgctgcct aatcccatgc      420
gggatgccga tcttcggatg tcccacgatg atatcatata gatatataaa ggaaccccccg    480 tctggcatct caatcctggg gaggaatgac ggagagagca cattcaacag acagcacaag     540
atcttcgttc tcgggtgcaa ccgagcatca tcgccatgac cgtcctcacc tcacctctgg     600
ccagctataa tgtggccaac aagctgtaca aaaccactct gctcaacacc gtctgcctcg     660
tggccggact gtcgatcttc ttcttcggct atgatcaggg attgatgggc ggtgttaaca     720
cgacgcgcga ctatgccgag cgcatgggct ttggccactg gacgaagac cagaacattg      780 tcgtcgtcga taagccgctg ctgcaggcg gtatcgtagc tgtctactat ctccccggaa      840
cgctgtgcgg ttgtctgctt ggcggttggc ttggtgatcg ctatggccgt atcaaaacaa     900
ttgccattgc ctgtgcgtgg agtgtctgcg cagccgccct gcaggcctca gctatgaatg     960
cgaactggat gttttgcggt atgtcgatga ttcttggaca atcacaaccg aactattact    1020
gatgatgaga tgaaacagcc cgcgttctga acggcgtcgg cactggaatc ttgaacgcaa    1080
tcacgcctgt gtgggcaacc gagactgctg ctcacacttc tcgaggccag ttcgttttca    1140
ttgagttcac cctcaacatt cttggtgttg ttgtagccta ctggctggaa ttgtacgtgc    1200
ctcctcactc aggatcccca gtcttgtgga aagtctccct aatgcggtgg cagtggtact    1260
tctaaatatc acgacaacac atcctccttc atctggagat tcccggtcgc cttccagatc    1320 ctcccccctaa tccttctgtt cctcatcatc tggatcatgc ctgaatcccc ccgctggctc    1380
gtcaaagtgg gtcgtgaaga agaggctcgc ttcatccttg gtcgtctccg tggcaatgag    1440
ggcgaggacg gcctcaaggc ggaagcagag tacaatgata ttgtcaacat ccacaagctt    1500
gaagtagaca ccgccaagca gcagagctac ttctccatgt tctttggcat tgggtctgga    1560
aagctacaca ctggccggcg cgtgcagctg gtcatctggc tccagatatt gcaagagtgg    1620
atcggtattg cggaaatcac catttacggc cctgagatct ttacgattgc tggcatcagc    1680
gcaaaggaca gactctgggt tagcgggatc aacaatatca catacatggt acgtttagcc    1740
aacacctcct cacctcaaag attccatcac actaacacgg gagcagttcg ccacactgat    1800
ctgcgtcttc accatcgatc gcataggtcg ccgttggact ctgtactggg gagctgtcgg    1860
ccagggcatt tgcatgttcg tcgccggtgg cctcgctcgc gcaaccatca atgcctcagg    1920
caaagcaagc cagagccaca tcggcggcgc tgcaacattc tttgtgttcc tctacactgc    1980
cattttcggc gctacctggc tgctacctgg ctgacggttc cttggttgta tccggccgag    2040
attttccctc tgcaggttag agccaaggga aatgcctggg gtgtcgttgg ctggtccatt    2100
ggcaacggct ggtgtgtaag tgcactttc attctcctct cccgtctggg ctcttctggt     2160
ctaatcttct ctaggtgctc ctgcttccta cgatcttcaa ggcgctcaac gaaaagacac    2220
tctacatttt tggcgccgtc aacgccctgt ccatcctcgt cgtgtgggct ctgtaccccg    2280
aatcgaatca acgaactcta gaggagatgg acctcgtctt tgctagcgac agcatctggg    2340
cctgggaggc tgagcgtaat tttgccaagc tcaaggctga aaacccggat cttgttcagg    2400
gctcaacaaa ccacggagtt gtagatattg agcaagttgc cgagccaaag gagtaggttc    2460
gtcgacaaga acttgacggt ctctttatac ataattttc ctactagcgg ccgcctagtc     2520
atcattggat aggcagatta ctcagcctga atgacatcaa catgttaccc atgatacaat    2580
```

-continued

| | |
|---|---|
| aggtcacaca aacaagcgct aagatgcact tggtatgaca agcccagtag tccgtttcaa | 2640 |
| aagacctaga tgatgaacta caacatgagg tgttgcctcc tgatccagtc caactgcaaa | 2700 |
| cgctgatgta tactcaatca agcctgatgt aaatgctgcg actcgattcg ctggatatga | 2760 |
| agatcaaaga gagctctgat gggtccaata tagccgggtt ttgttaggac agtccaccac | 2820 |
| accgatatta gaattggtca agcaccttat catttcatag agattgcggt ttctagatct | 2880 |
| acgccaggac cgagcaagcc cagatgagaa ccgacgcaga tttccttggc acctgttgct | 2940 |
| tcagctgaat cctggcaata cgagatacct gctttgaata ttttgaatag ctcgcccgct | 3000 |
| ggagagcatc ctgaatgcaa gtaacaaccg tagaggctga cacggcaggt gttgctaggg | 3060 |
| agcgtcgtgt tctacaaggc cagacgtctt cgcggttgat atatatgtat gtttgactgc | 3120 |
| aggctgctca gcgacgacag tcaagttcgc cctcgctgct tgtgcaataa tcgcagtggg | 3180 |
| gaagccacac cgtgactccc atctttcagt aaagctctgt tggtgtttat cagcaataca | 3240 |
| cgtaatttaa actcgttagc atggggctga tagcttaatt accgtttacc agtgccgcgg | 3300 |
| ttctgcagct ttccttggcc cgtaaaattc ggcgaagcca gccaatcacc agctaggcac | 3360 |
| cagctaaacc ctataattag tctcttatca acaccatccg ctcccccggg atcaatgagg | 3420 |
| agaatgaggg ggatgcgggg ctaaagaagc ctacataacc ctcatgccaa ctcccagttt | 3480 |
| acactcgtcg agccaacatc ctgactataa gctaacacag aatgcctcaa tcctgggaag | 3540 |
| aactggccgt tgataagcgc gcccgcctcg caaaaaccat ccctgatgaa tggaaagtcc | 3600 |
| agacgctgcc tgcggaagac agcgttattg atttcccaaa gaaatcgggc atcctttcag | 3660 |
| aggccgaact gaagatcaca gaggcctccg ctgcagatct tgtgtccaag ctggcggccg | 3720 |
| gagagttgac ctcggtggaa gttacgctag cattctgtaa acgggcagca atcgcccagc | 3780 |
| agttagtagg gtcccctcta cctctcaggg agatgtaaca acgccacctt atgggactat | 3840 |
| caagctgacg ctggcttctg tgcagacaaa ctgcgcccac gagttcttcc ctgacgccgc | 3900 |
| tctcgcgcag gcaagggaac tcgatgaata ctacgcaaag cacaagagac ccgttggtcc | 3960 |
| actccatggc ctcccccatct ctctcaaaga ccagcttcga gtcaaggtac accgttgccc | 4020 |
| ctaagtcgtt agatgtccct ttttgtcagc taacatatgc caccagggct acgaaacatc | 4080 |
| aatgggctac atctcatggc taaacaagta cgacgaaggg gactcggttc tgacaaccat | 4140 |
| gctccgcaaa gccggtgccg tcttctacgt caagacctct gtcccgcaga ccctgatggt | 4200 |
| ctgcgagaca gtcaacaaca tcatcgggcg caccgtcaac ccacgcaaca agaactggtc | 4260 |
| gtgcggcggc agttctggtg gtgagggtgc gatcgttggg attcgtggtg gcgtcatcgg | 4320 |
| tgtaggaacg gatatcggtg gctcgattcg agtgccggcc gcgttcaact tcctgtacgg | 4380 |
| tctaaggccg agtcatggcc ggctgccgta tgcaaagatg gcgaacagca tggagggtca | 4440 |
| ggagacggtg cacagcgttg tcgggccgat tacgcactct gttgagggtg agtccttcgc | 4500 |
| ctcttccttc ttttcctgct ctataccagg cctccactgt cctcctttct tgctttttat | 4560 |
| actatatacg agaccggcag tcactgatga agtatgttag acctccgcct cttcaccaaa | 4620 |
| tccgtcctcg gtcaggagcc atggaaatac gactccaagg tcatccccat gccctggcgc | 4680 |
| cagtccgagt cggacattat tgcctccaag atcaagaacg gcgggctcaa tatcggctac | 4740 |
| tacaacttcg acggcaatgt ccttccacac cctcctatcc tgcgcggcgt ggaaaccacc | 4800 |
| gtcgccgcac tcgccaaagc cggtcacacc gtgaccccgt ggacgccata caagcacgat | 4860 |
| ttcgccacac atctcatctc ccatatctac gcggctgacg gcagcgccga cgtaatgcgc | 4920 |
| gatatcagtg catccggcga gccggcgatt ccaaatatca aagacctact gaacccgaac | 4980 |

```
atcaaagctg ttaacatgaa cgagctctgg gacacgcatc tccagaagtg gaattaccag    5040
atggagtacc ttgagaaatg gcgggaggct gaagaaaagg ccgggaagga actggacgcc    5100
atcatcgcgc cgattacgcc taccgctgcg gtacggcatg accagttccg gtactatggg    5160
tatgcctctg tgatcaacct gctggatttc acgagcgtgg ttgttccggt tacctttgcg    5220
gataagaaca tcgataagaa gaatgagagt ttcaaggcgg ttagtgagct tgatgccctc    5280
gtgcaggaag agtatgatcc ggaggcgtac catggggcac cggttgcagt gcaggttatc    5340
ggacggagac tcagtgaaga gaggacgttg gcgattgcag aggaagtggg gaagttgctg    5400
ggaaatgtgg tgactccata gctaataagt gtcagatagc aatttgcaca agaaatcaat    5460
accagcaact gtaaataagc gctgaagtga ccatgccatg ctacgaaaga gcagaaaaaa    5520
acctgccgta gaaccgaaga gatatgacac gcttccatct ctcaaaggaa gaatcccttc    5580
agggttgcgt ttccagtcta gacgcgtctc gcatcaaact atttcggcac gtggacacat    5640
tgtccgctgg agctgggcat gtgtttaaac caacctcgat tacctcacac tggcggcagc    5700
aatgaatcaa catatctcaa gtacaagaga tgcagcagct gagtacctgt atatcatatc    5760
tcatacattt caaatcccat cagtcatcag gccccagccc agtatcgatc ccaggcatct    5820
cggcagatgt cattttgcag atgcttcaga aagtcgtcaa acttgacagg ctcttctcct    5880
tccaatctca tcactccatc cttgatcccc tgccatccct ccacaggcaa tttgatgtaa    5940
ctgtgcctct tgtcgcagaa gtgcatgacg gcgggcgatc ccaccgtctc aggatcatgt    6000 cgggcccttgt agcaaagctc gcagattagg gtggttgaac attctgtaca ataatgaacc    6060
acagaatgtc cccaccaggc aaatgcagcc acggggttac agatgccacc gtcgcaactg    6120
caaacgacta tctcggggtt cccaagatct ccctcgtctc tcggtgacga cttcttgcca    6180
ctcctaatac tggccatggt ttcgtagggg gctagcccct caattgtccc aaccatcttg    6240
atagctacta caccttccga gtctgtatct tcagtatctt catcgtcgct ttcatcatca    6300
tcgcttctgt cgctggactg atttgctctc tcccaaagct cgagttcctc ctccgtgaca    6360
tgagtgattt tggagaacat tgctgatatg acgatgcgcg catagcgctg tatatcttgt    6420
ccttccggta gagctttgct tagcaccatt agggcatggg ccagcttttc catattttgt    6480
ccatcgttcc aagacacttt atcggttagg cctgcaaagc aatcatctag gacgctttgg    6540
agtctttcct gaaactcact tgcctgtccc atctttagac acattgacgc aagaacaatg    6600
cggcgataga ccaggtctag actcgtatag atcggcaccg acagagaaag cggcctgttc    6660
atgatgtttt tgagtgactc gagggcctct tgcttaacct tgggatctcg cgagccccgg    6720
aaaatttcgt agagaacatc agacatgaca tttaccagtc gctgcatcat ggtctgcggc    6780
tcctcgtccg tgatagagta cggatacccg cccgaggtgc tggcgaatat ctcatccagg    6840
gtcttgcgag cattctccaa atctcccttg gctctgaaat aagtaaccgc taactcaaga    6900
cgcagcggag caccagagtt gagccggtcg agaaaccgaa tagcatcctg ataggcatca    6960
atcagaaagt cgacttcgcc ctctcttatt gcgagggagc gaagcttgtc atgccgctca    7020
tgtccctggt tgcaatagtt ccacgccatc caggtcagtc tgtcaatagg actccagctc    7080
ttcagcgtcc gaaaatatcc agcgtaaatt taaat                              7115

<210> SEQ ID NO 4
<211> LENGTH: 2514
<212> TYPE: DNA
<213> ORGANISM: Artificial Sequence
<220> FEATURE:
```

<223> OTHER INFORMATION: DNA fragment for transformation.

<400> SEQUENCE: 4

| | | | | | |
|---|---|---|---|---|---|
| cttaaggacc | ggtggtgatg | gcttagagct | ccaccgactc | gtcccagttc | ttgactcagg | 60 |
| cccacggaca | tcattggtgc | gcataataac | cgacaaaagc | cggagcgatc | gacagacgtg | 120 |
| ccgatggcgc | gcgttgctgg | gctgtcaacg | ctccctgagg | gctgtaacag | agtgacgaca | 180 |
| agaacagtat | tccgggcata | ctagtatcag | ccagctccag | cttttcccca | tggagaaccc | 240 |
| caaactggag | gcttctcttg | cgataccatc | tcatcattgg | acagcgaccg | gatggctccg | 300 |
| acgaagcgtt | taagcgtctc | agctggcgaa | tgggatcccc | tcattctgaa | cagggagccc | 360 |
| gttttaggat | accatttcct | tcggaaacga | tgagcttttt | gatgctgcct | aatcccatgc | 420 |
| gggatgccga | tcttcggatg | tcccacgatg | atatcatata | gatatataaa | ggaaccccccg | 480 |
| tctggcatct | caatcctggg | gaggaatgac | ggagagagca | cattcaacag | acagcacaag | 540 |
| atcttcgttc | tcgggtgcaa | ccgagcatca | tcgccatgac | cgtcctcacc | tcacctctgg | 600 |
| ccagctataa | tgtggccaac | aagctgtaca | aaaccactct | gctcaacacc | gtctgcctcg | 660 |
| tggccggact | gtcgatcttc | ttcttcggct | atgatcaggg | attgatgggc | ggtgttaaca | 720 |
| cgacgcgcga | ctatgccgag | cgcatgggct | ttggccactg | ggacgaagac | cagaacattg | 780 |
| tcgtcgtcga | taagccgctg | ctgcagggcg | gtatcgtagc | tgtctactat | ctccccggaa | 840 |
| cgctgtgcgg | ttgtctgctt | ggcggttggc | ttggtgatcg | ctatggccgt | atcaaaacaa | 900 |
| ttgccattgc | ctgtgcgtgg | agtgtctgcg | cagccgccct | gcaggcctca | gctatgaatg | 960 |
| cgaactggat | gttttgcggt | atgtcgatga | ttcttggaca | atcacaaccg | aactattact | 1020 |
| gatgatgaga | tgaaacagcc | cgcgttctga | acggcgtcgg | cactggaatc | ttgaacgcaa | 1080 |
| tcacgcctgt | gtgggcaacc | gagactgctg | ctcacacttc | tcgaggccag | ttcgtttcca | 1140 |
| ttgagttcac | cctcaacatt | cttggtgttg | ttgtagccta | ctggctggaa | ttgtacgtgc | 1200 |
| ctcctcactc | aggatcccca | gtcttgtgga | aagtctccct | aatgcggtgg | cagtggtact | 1260 |
| tctaaatatc | acgacaacac | atcctccttc | atctggagat | tcccggtcgc | cttccagatc | 1320 |
| ctcccccctaa | tccttctgtt | cctcatcatc | tggatcatgc | ctgaatcccc | ccgctggctc | 1380 |
| gtcaaagtgg | gtcgtgaaga | agaggctcgc | ttcatccttg | gtcgtctccg | tggcaatgag | 1440 |
| ggcgaggacg | gcctcaaggc | ggaagcagag | tacaatgata | ttgtcaacat | ccacaagctt | 1500 |
| gaagtagaca | ccgccaagca | gcagagctac | ttctccatgt | tctttggcat | tgggtctgga | 1560 |
| aagctacaca | ctggccggcg | cgtgcagctg | gtcatctggc | tccagatatt | gcaagagtgg | 1620 |
| atcggtattg | cgggaatcac | catttacggc | cctgagatct | ttacgattgc | tggcatcagc | 1680 |
| gcaaaggaca | gactctgggt | tagcgggatc | aacaatatca | catacatggt | acgtttagcc | 1740 |
| aacacctcct | cacctcaaag | attccatcac | actaacacgg | gagcagttcg | ccacactgat | 1800 |
| ctgcgtcttc | accatcgatc | gcataggtcg | ccgttggact | ctgtactggg | gagctgtcgg | 1860 |
| ccagggcatt | tgcatgttcg | tcgccggtgg | cctcgctcgc | gcaaccatca | atgcctcagg | 1920 |
| caaagcaagc | cagagccaca | tcggcggcgc | tgcaacattc | tttgtgttcc | tctacactgc | 1980 |
| cattttcggc | gctacctggc | tgctacctgg | ctgacggttc | cttggttgta | tccggccgag | 2040 |
| attttccctc | tgcaggttag | agccaaggga | aatgcctggg | gtgtcgttgg | ctggtccatt | 2100 |
| ggcaacggct | ggtgtgtaag | tgcacttttc | attctcctct | cccgtctggg | ctcttctggt | 2160 |
| ctaatcttct | ctaggtgctc | ctgcttccta | cgatcttcaa | ggcgctcaac | gaaaagacac | 2220 |
| tctacatttt | tggcgccgtc | aacgccctgt | ccatcctcgt | cgtgtgggct | ctgtaccccg | 2280 |

```
aatcgaatca acgaactcta gaggagatgg acctcgtctt tgctagcgac agcatctggg    2340
cctgggaggc tgagcgtaat tttgccaagc tcaaggctga aaacccggat cttgttcagg    2400
gctcaacaaa ccacggagtt gtagatattg agcaagttgc cgagccaaag gagtaggttc    2460
gtcgacaaga acttgacggt ctctttatac ataattttc ctactagcgg ccgc          2514
```

<210> SEQ ID NO 5
<211> LENGTH: 32
<212> TYPE: DNA
<213> ORGANISM: Artificial Sequence
<220> FEATURE:
<223> OTHER INFORMATION: Oligo DNA for PCR.

<400> SEQUENCE: 5

```
atacgcgtct cgcatcaaac tatttcggca cg                                    32
```

<210> SEQ ID NO 6
<211> LENGTH: 39
<212> TYPE: DNA
<213> ORGANISM: Artificial Sequence
<220> FEATURE:
<223> OTHER INFORMATION: Oligo DNA for PCR.

<400> SEQUENCE: 6

```
atgcatattt aaatttacgc tggatattt cggacgctg                              39
```

<210> SEQ ID NO 7
<211> LENGTH: 3127
<212> TYPE: DNA
<213> ORGANISM: Artificial Sequence
<220> FEATURE:
<223> OTHER INFORMATION: DNA fragment for transformation.

<400> SEQUENCE: 7

```
agtgtctcaa tattgaagga accttgatcg gctacgactt gggatggaaa agacatggtc      60
cgccgctata cagaagagac gcggatacag taaatacata gtgcgccaat ataggtgcgt     120
atgatagaat aaagcagggg caagaagcac aataatacta ttgttcgatc taaaatggtg     180 tcgaaaaga acgccccgtt gactgcgagc ttgactgcaa gcttggctgc agcatgtgac      240
tcggaagagc ttactcacca ggatcgaacc gggcgaatca tacgctgtcc ttctcttggt     300
gtactctgcc cacttcgtat gacacgagca gacaaggctg ctcctcatac tactaatagc     360
agtagtgatt ctgaaaacct ggggatcgtg atgatgattg gtgcgcatgg ctgccgtatt     420
gggcctgtgg attctcagcg gagatcagct tcgacaagtg accggtggtg atggcttaga     480
gctccaccga ctcgtcccag ttcttgactc aggcccacgg acatcattgg tgcgcataat     540
aaccgacaaa agccggagcg atcgacagac gtgccgatgg cgcgcgttgc tgggctgtca     600
acgctccctg agggctgtaa cagagtgacg acaagaacag tattccgggc atactagtat     660
cagccagctc cagcttttcc ccatggagaa ccccaaactg gaggcttctc ttgcgatacc     720
atctcatcat tggacagcga ccggatggct ccgacgaagc gtttaagcgt ctcagctggc     780
gaatgggatc ccctcattct gaacagggag cccgttttag gataccattt ccttcggaaa     840
cgatgagctt tttgatgctg cctaatccca tgcgggatgc cgatcttcgg atgtcccacg     900
atgatatcat atagatatat aaaggaaccc ccgtctggca tctcaatcct ggggaggaat     960
gacggagaga gcacattcaa cagacagcac aagatcttcg ttctcgggtg caaccgagca    1020
tcatcgccat gaccgtcctc acctcacctc tggccagcta taatgtggcc aacaagctgt    1080
```

```
acaaaaccac tctgctcaac accgtctgcc tcgtggccgg actgtcgatc ttcttcttcg   1140
gctatgatca gggattgatg ggcggtgtta cacgacgcg cgactatgcc gagcgcatgg    1200
gctttggcca ctgggacgaa gaccagaaca ttgtcgtcgt cgataagccg ctgctgcagg   1260
gcggtatcgt agctgtctac tatctccccg gaacgctgtg cggttgtctg cttggcggtt   1320
ggcttggtga tcgctatggc cgtatcaaaa caattgccat tgcctgtgcg tggagtgtct   1380
gcgcagccgc cctgcaggcc tcagctatga atgcgaactg gatgttttgc ggtatgtcga   1440
tgattcttgg acaatcacaa ccgaactatt actgatgatg agatgaaaca gcccgcgttc   1500
tgaacggcgt cggcactgga atcttgaacg caatcacgcc tgtgtgggca accgagactg   1560
ctgctcacac ttctcgaggc cagttcgttt ccattgagtt caccctcaac attcttggtg   1620
ttgttgtagc ctactggctg gaattgtacg tgcctcctca ctcaggatcc ccagtcttgt   1680
ggaaagtctc cctaatgcgg tggcagtggt acttctaaat atcacgacaa cacatcctcc   1740
ttcatctgga gattcccggt cgccttccag atcctccccc taatccttct gttcctcatc   1800
atctggatca tgcctgaatc cccccgctgg ctcgtcaaag tgggtcgtga agaagaggct   1860
cgcttcatcc ttggtcgtct ccgtggcaat gagggcgagg acggcctcaa ggcggaagca   1920
gagtacaatg atattgtcaa catccacaag cttgaagtag acaccgccaa gcagcagagc   1980
tacttctcca tgttctttgg cattgggtct ggaaagctac acactggccg gcgcgtgcag   2040
ctggtcatct ggctccagat attgcaagag tggatcggta ttgcgggaat caccatttac   2100
ggccctgaga tctttacgat tgctggcatc agcgcaaagg acagactctg ggttagcggg   2160
atcaacaata tcacatacat ggtacgttta gccaacacct cctcacctca aagattccat   2220
cacactaaca cgggagcagt tcgccacact gatctgcgtc ttcaccatcg atcgcatagg   2280
tcgccgttgg actctgtact ggggagctgt cggccagggc atttgcatgt tcgtcgccgg   2340
tggcctcgct cgcgcaacca tcaatgcctc aggcaaagca agccagagcc acatcggcgg   2400
cgctgcaaca ttctttgtgt tcctctacac tgccattttc ggcgctacct ggctgacggt   2460
tccttggttg tatccggccg agattttccc tctgcaggtt agagccaagg gaaatgcctg   2520
gggtgtcgtt ggctggtcca ttggcaacgg ctggtgtgta agtgcacttt tcattctcct   2580
ctcccgtctg ggctcttctg gtctaatctt ctctaggtgc tcctgcttcc tacgatcttc   2640
aaggcgctca acgaaaagac actctacatt tttggcgccg tcaacgccct gtccatcctc   2700
gtcgtgtggg ctctgtaccc cgaatcgaat caacgaactc tagaggagat ggacctcgtc   2760
tttgctagcg acagcatctg ggcctgggag gctgagcgta attttgccaa gctcaaggct   2820
gaaaacccgg atcttgttca gggctcaaca aaccacggag ttgtagatat tgagcaagtt   2880
gccgagccaa aggagtaggt tcgtcgacaa gaacttgacg gtctctttat acataatttt   2940
tcctactact cgcatcaaac tatttcggca cgtggacaca ttgtccgctg gagctgggca   3000
tgtgttaaaa ccaaccctcga ttacctcaca ctggcggcag caatgaatca acatatctca   3060
agtacaagag atgcagcagc tgagtacctg tatatcatat ctcatacatt tcaaatccca   3120
tcagtca                                                            3127
```

<210> SEQ ID NO 8
<211> LENGTH: 859
<212> TYPE: PRT
<213> ORGANISM: Trichoderma reesei

<400> SEQUENCE: 8

Met Pro His Arg Glu Arg Gly Lys Gln Arg Glu Gly Gly Asp Ser Tyr

```
1               5                   10                  15
Arg Pro Ser Arg Pro Ala Arg Ser Arg Ser Arg Ser Arg Ser Pro Pro
                20                  25                  30
Arg Ala Pro Val Pro Val Arg Thr Glu Glu Lys Gln Ala Ala Ala
                35                  40                  45
Lys Ala Glu Tyr Glu Lys Leu Leu Asn Met Arg Ser Gly Gly Thr Tyr
                50                  55                  60
Ile Pro Pro Ala Arg Leu Arg Ala Leu Gln Ala Gln Ile Thr Asp Lys
65                  70                  75                  80
Ser Ser Lys Glu Tyr Gln Arg Met Ala Trp Glu Ala Leu Lys Lys Ser
                    85                  90                  95
Ile Asn Gly Leu Ile Asn Lys Val Asn Thr Ala Asn Ile Lys His Ile
                100                 105                 110
Val Pro Glu Leu Phe Gly Glu Asn Leu Val Arg Gly Arg Gly Leu Phe
                115                 120                 125
Cys Arg Ser Ile Met Lys Ala Gln Ala Ala Ser Leu Pro Phe Thr Pro
        130                 135                 140
Ile Tyr Ala Ala Met Ala Ala Ile Val Asn Thr Lys Leu Pro Gln Val
145                 150                 155                 160
Gly Glu Leu Leu Val Lys Arg Leu Ile Met Gln Phe Arg Lys Gly Phe
                    165                 170                 175
Lys Arg Asn Asp Lys Ala Val Cys Leu Ser Ser Thr Phe Leu Ala
        180                 185                 190
His Leu Ile Asn Gln Gln Val Gln His Glu Met Leu Ala Gly Gln Ile
                195                 200                 205
Leu Leu Leu Leu Leu His Lys Pro Thr Asp Asp Ser Val Glu Ile Ala
        210                 215                 220
Val Gly Phe Cys Lys Glu Val Gly Gln Tyr Leu Glu Glu Met Gln Pro
225                 230                 235                 240
Ala Ile Ser Met Ala Val Phe Asp Gln Phe Arg Asn Ile Leu His Glu
                245                 250                 255
Ser Asp Ile Asp Lys Arg Thr Gln Tyr Met Ile Glu Val Leu Phe Gln
                260                 265                 270
Ile Arg Lys Asp Lys Phe Lys Asp His Pro Ala Ile Lys Glu Glu Leu
        275                 280                 285
Asp Leu Val Glu Glu Asp Gln Ile Thr His Lys Val Glu Leu Asp
        290                 295                 300
Gly Glu Ile Asp Val Gln Asp Gly Leu Asn Ile Phe Lys Tyr Asp Pro
305                 310                 315                 320
Glu Trp Glu Glu His Glu Glu Ala Tyr Lys Arg Leu Lys Ala Glu Ile
                    325                 330                 335
Leu Gly Glu Ala Ser Asp Asp Glu Gly Asp Glu Asp Glu
                340                 345                 350
Asp Glu Ser Ser Glu Asp Glu Glu Asn Glu Glu Thr Lys Ala Met Glu
                355                 360                 365
Ile Lys Asp Gln Ser Asn Ala Asp Leu Val Asn Leu Arg Arg Thr Ile
        370                 375                 380
Tyr Leu Thr Ile Met Ser Ser Ala Asp Pro Glu Glu Ala Val His Lys
385                 390                 395                 400
Leu Met Lys Ile Asn Leu Pro Val Gly Gln Glu Pro Glu Leu Pro Ser
                    405                 410                 415
Met Ile Val Glu Cys Cys Ser Gln Glu Lys Thr Tyr Thr Lys Phe Phe
                420                 425                 430
```

```
Gly Leu Ile Gly Glu Arg Phe Ala Lys Ile Asn Arg Leu Trp Cys Asp
        435                 440                 445

Leu Phe Glu Gln Ala Phe Val Lys Tyr Tyr Glu Thr Ile His Arg Tyr
450                 455                 460

Glu Asn Asn Lys Leu Arg Asn Ile Ala Met Leu Phe Gly His Met Phe
465                 470                 475                 480

Ala Ser Asp Ala Leu Gly Trp His Cys Leu Ser Val Ile His Leu Asn
                485                 490                 495

Glu Glu Glu Thr Thr Ser Ser Arg Ile Phe Ile Lys Ile Leu Phe
                500                 505                 510

Gln His Ile Ser Glu Glu Ile Gly Leu Ala Lys Leu Arg Ala Arg Met
        515                 520                 525

Thr Asp Glu Thr Leu Arg Pro Ser Leu Glu Gly Leu Phe Pro Arg Glu
        530                 535                 540

Asn Pro Arg Asn Ile Arg Phe Ser Ile Asn Tyr Phe Thr Ser Ile Gly
545                 550                 555                 560

Met Gly Val Leu Thr Glu Glu Met Arg Glu His Leu Met Asn Met Pro
                565                 570                 575

Lys Pro Ala Leu Pro Ala Pro Ala Ala Gln Asp Arg Ser Asp Thr Asp
                580                 585                 590

Ser Val Ser Ser Tyr Ser Ser Tyr Thr His Ser Ser Tyr Ser Ser Arg
        595                 600                 605

Ser Arg Ser Arg Ser Arg Ser Val Gly Arg Arg Ser Gly Gly Arg Gly
        610                 615                 620

Arg Ser Leu Ser Arg Thr Pro Pro Arg Arg Gly Ala Arg Ser Arg Ser
625                 630                 635                 640

Tyr Ser Asp Asp Ser Arg Ser Pro Ser Arg Ser Arg Ser Arg Ser Arg
                645                 650                 655

Ser Asp Ser Val Ser Thr Arg Gly Arg Arg Ala Ser Tyr Ser Ala
                660                 665                 670

Ser Pro Pro Arg Arg Gly Gly Arg Arg Val Ala Ser Arg Ser Arg Ser
        675                 680                 685

Tyr Ser Ser Gly Ser Ser Arg Ser Pro Pro Arg Asn Arg Gly Arg
        690                 695                 700

Ala Arg Ser Asn Ser Tyr Ser Ser Tyr Ser Arg Ser Pro Ser Ser Ser
705                 710                 715                 720

Pro Arg Arg Gly Arg Asp Ala Asp Ser Ala Ser Pro Pro Arg Arg
                725                 730                 735

Gly Arg Pro Arg Gln Ser Pro Pro Gly Pro Ala Gly Arg Arg Asn
                740                 745                 750

Ser Ser Ser Val Gly Ser Gly Gly Pro Arg Lys Lys Pro Arg Arg Asp
        755                 760                 765

Ser Arg Ser Pro Ser Arg Asp Tyr Ser Arg Ser Pro Ser Arg Ser
        770                 775                 780

Pro Ser Arg Ser Arg Ser Pro Pro Ala Ala Arg Gly Arg Arg Gly
785                 790                 795                 800

Ser Tyr Thr Pro Ser Arg Ser Arg Ser Pro Pro Arg Arg Val Arg
                805                 810                 815

Asp Gly Ser Pro Gly Arg Leu Arg Gly Gly Arg Ser Pro Ser Pro Pro
                820                 825                 830

Leu Pro Val Lys Arg Arg Tyr Asp Ser Glu Ser Val Ser Arg Ser
                835                 840                 845
```

Pro Pro Pro Leu Lys Arg Gly Arg Arg Asp Asn
    850                 855

<210> SEQ ID NO 9
<211> LENGTH: 2580
<212> TYPE: DNA
<213> ORGANISM: Trichoderma reesei

<400> SEQUENCE: 9

| | | | | | |
|---|---|---|---|---|---|
| atgccgcacc | gcgagcgcgg | caagcagcga | gaaggcggcg | actcgtaccg | cccctcgagg | 60 |
| ccagcgcgtt | cacgctcgcg | ctcgcgatcg | ccgcctcgcg | cgccggtgcc | cgtgcggacg | 120 |
| gaggaggaga | agcaggcggc | ggcaaaggcc | gagtacgaga | agctgctcaa | catgcggtcg | 180 |
| ggcggcacgt | acatcccgcc | ggcgaggctg | agggcgctgc | aggcgcagat | cacggacaag | 240 |
| agcagcaagg | agtaccagcg | gatggcgtgg | gaggcgctca | agaagagcat | caacggcctg | 300 |
| atcaacaagg | tcaacacggc | caacatcaag | cacattgtgc | ccgagctgtt | tggcgagaac | 360 |
| ctggtgcgcg | gccgcggcct | cttctgccgc | tccatcatga | aggcccaggc | cgccagtttg | 420 |
| cccttcacgc | ccatctacgc | cgccatggcc | gccattgtca | caccaagct | gccgcaggtc | 480 |
| ggcgagctgc | tggtcaagcg | cctcatcatg | cagttccgca | agggcttcaa | gcgcaacgac | 540 |
| aaggccgtct | gtctgtcgtc | gaccaccttc | ctcgcccacc | tcatcaacca | gcaggtgcag | 600 |
| cacgagatgc | tggccggcca | gatcctgctg | ctgctgctgc | acaagccgac | cgacgacagc | 660 |
| gtcgagattg | ccgtgggctt | ctgcaaggag | gttggccagt | acctcgagga | gatgcagcct | 720 |
| gccatttcca | tggccgtctt | cgaccagttc | cgcaacatcc | tccacgagtc | cgacattgac | 780 |
| aagcgaacgc | agtacatgat | tgaggtgctc | ttccagatca | ggaaggacaa | gttcaaggat | 840 |
| cacccggcca | tcaaggagga | gctggacttg | gtggaggagg | aggaccagat | cacgcacaag | 900 |
| gtggagcttg | atggcgagat | tgatgtgcag | gacggactca | acatcttcaa | gtacgacccg | 960 |
| gagtgggagg | agcatgagga | ggcatacaag | aggctcaagg | cggagattct | gggcgaagcc | 1020 |
| agcgatgacg | aggagggcga | cgaggacgag | gacgaggacg | agagctccga | agatgaagaa | 1080 |
| aacgaagaga | caaaggccat | ggagatcaag | gaccagtcta | acgccgactt | ggtcaaccta | 1140 |
| cggaggacca | tctacctcac | catcatgtcg | agcgccgacc | cagaggaagc | agttcacaag | 1200 |
| ctgatgaaga | tcaacctgcc | cgtcggccag | gaacccgagc | tgccctcgat | gattgtcgag | 1260 |
| tgttgctcgc | aggagaagac | gtacaccaag | ttctttggct | tgatcggcga | gcgtttcgcc | 1320 |
| aagatcaatc | ggctgtggtg | cgacctcttt | gagcaggcct | ttgtcaagta | ctacgagacg | 1380 |
| atccaccgat | acgaaaacaa | caagctgcga | acattgcca | tgctgtttgg | ccacatgttt | 1440 |
| gcttccgacg | ctctgggctg | gcactgcctt | ccgtcattc | acctcaacga | ggaggagacc | 1500 |
| acgtcgagca | gccgcatctt | catcaagatt | ctgttccagc | acatttccga | ggaaatcggc | 1560 |
| ctggctaagc | tccgggcacg | catgactgac | gagacgctgc | ggcccagcct | cgaaggcctc | 1620 |
| ttccccagag | agaaccctcg | caacatccga | ttctccatca | actacttcac | cagcatcggc | 1680 |
| atgggtgtac | tgaccgagga | gatgcgagag | cacctcatga | acatgcccaa | gctgcgctg | 1740 |
| cccgcccctg | ctgctcagga | ccgctcggat | acggactccg | tctcgagcta | ttcgtcttac | 1800 |
| actcactcat | catactcttc | ccgctcgcgc | tcacggtccc | gatctgtggg | tcgtcggagc | 1860 |
| ggcggtcgag | gccgatcgct | ttcccgaact | ccgcctcgac | gtggcgcaag | gagccgatcc | 1920 |
| tactctgacg | actcacggtc | accgtcgcgg | tcaagatcac | gatcccgctc | cgattccgtc | 1980 |
| tctactcgtg | ggcgaaggcg | agcgtcgtac | tcggccagtc | ctccccggcg | tggtggccgt | 2040 |

-continued

| | |
|---|---|
| cgggttgcca gcagaagccg aagctactcg tcgggctcct cacggtctcc gccaccacgg | 2100 |
| aaccgcggtc gcgcacgaag caactcgtat agttcctaca gccgctctcc atcttcttca | 2160 |
| ccacgacgcg gcagagacgc agactcggcc agcccgcctc cgcgaagggg tcgaccgcgc | 2220 |
| cagagcccac caggcggtcc cgcaggtcga aggaacagct cgtctgtcgg cagcggaggg | 2280 |
| ccccgcaaga agccccgacg ggacagccga tcgccgtctc gcgactattc gtcccggtcc | 2340 |
| ccgtctcggt cgccgtcgag atctcgatcg cctccgccgg ctgcgcgtgg ccgaaggggc | 2400 |
| tcttatacgc cgtcacgcag ccgcagcccg cctccgcgca gggtgaggga tggctcgccg | 2460 |
| ggtcgtctga ggggtgggag gtcgcctagt cctcctttgc cggtgaagag gaggcggtat | 2520 |
| gatagcgaga gtgtttctcg gtcgccgcct cctttgaagc gcgggagaag ggataactaa | 2580 |

<210> SEQ ID NO 10
<211> LENGTH: 5789
<212> TYPE: DNA
<213> ORGANISM: Artificial Sequence
<220> FEATURE:
<223> OTHER INFORMATION: DNA fragment for transformation.

<400> SEQUENCE: 10

| | |
|---|---|
| cttaagggtg cgtatgatag aataaagcag gggcaagaag cacaataata ctattgttcg | 60 |
| atctaaaatg gtgtcgaaaa agaacgcccc gttgactgcg agcttgactg caagcttggc | 120 |
| tgcagcatgt gactcggaag agcttactca ccaggatcga accgggcgaa tcatacgctg | 180 |
| tccttctctt ggtgtactct gcccacttcg tatgacacga gcagacaagg ctgctcctca | 240 |
| tactactaat agcagtagtg attctgaaaa cctggggatc gtgatgatga ttggtgcgca | 300 |
| tggctgccgt attgggcctg tggattctca gcggagatca gcttcgacaa gtgaccggtg | 360 |
| gtgatggctt agagctccac cgactcgtcc cagttcttga ctcaggccca cggacatcat | 420 |
| tggtgcgcat aataaccgac aaaagccgga gcgatcgaca gacgtgccga tggcgcgcgt | 480 |
| tgctgggctg tcaacgctcc ctgagggctg taacagagtg acgacaagaa cagtattccg | 540 |
| ggcatactag tatcagccag ctccagcttt tccccatgga gaaccccaaa ctggaggctt | 600 |
| ctcttgcgat accatctcat cattggacag cgaccggatg gctccgacga agcgtttaag | 660 |
| cgtctcagct ggcgaatggg atcccctcat tctgaacagg gagcccgttt taggatacca | 720 |
| tttccttcgg aaacgatgag ctttttgatg ctgcctaatc ccatgcggga tgccgatctt | 780 |
| cggatgtccc acgatgatat catatagata tataaggaa ccccgtctg gcatctcaat | 840 |
| cctggggagg aatgacggag agagcacatt caacagacag cacaagatct tcgttctcgg | 900 |
| gtgcaaccga gcatcatcgc catgaccgtc ctcacctcac ctctggccag ctataatgtg | 960 |
| gccaacaagc tgtacaaaac cactctgctc aacaccgtct gcctcgtggc cggactgtcg | 1020 |
| atcttcttct tcggctatga tcagggattg atgggcggtg ttaacacgac gcgcgactat | 1080 |
| gccgagcgca tgggctttgg ccactgggac gaagaccaga acattgtcgt cgtcgataag | 1140 |
| ccgctgctgc agggcggtat cgtagctgtc tactatctcc ccggaacgct gtgcggttgt | 1200 |
| ctgcttggcg gttggcttgg tgatcgctat ggccgtatca aaacaattgc cattgcctgt | 1260 |
| gcgtggagtg tctgcgcagc cgccctgcag gcctcagcta tgaatgcgaa ctggatgttt | 1320 |
| tgcggtatgt cgatgattct tggacaatca caaccggcgg ccgcctagtc atcattggat | 1380 |
| aggcagatta ctcagcctga atgacatcaa catgttaccc atgatacaat aggtcacaca | 1440 |
| aacaagcgct aagatgcact tggtatgaca agcccagtag tccgtttcaa aagacctaga | 1500 |
| tgatgaacta caacatgagg tgttgcctcc tgatccagtc caactgcaaa cgctgatgta | 1560 |

```
tactcaatca agcctgatgt aaatgctgcg actcgattcg ctggatatga agatcaaaga      1620
gagctctgat gggtccaata tagccgggtt ttgttaggac agtccaccac accgatatta      1680
gaattggtca agcaccttat catttcatag agattgcggt ttctagatct acgccaggac      1740
cgagcaagcc cagatgagaa ccgacgcaga tttccttggc acctgttgct tcagctgaat      1800
cctggcaata cgagatacct gctttgaata ttttgaatag ctcgcccgct ggagagcatc      1860
ctgaatgcaa gtaacaaccg tagaggctga cacggcaggt gttgctaggg agcgtcgtgt      1920
tctacaaggc cagacgtctt cgcggttgat atatatgtat gtttgactgc aggctgctca      1980
gcgacgacag tcaagttcgc cctcgctgct tgtgcaataa tcgcagtggg gaagccacac      2040
cgtgactccc atctttcagt aaagctctgt tggtgtttat cagcaataca cgtaatttaa      2100
actcgttagc atggggctga tagcttaatt accgtttacc agtgccgcgg ttctgcagct      2160
ttccttggcc cgtaaaattc ggcgaagcca gccaatcacc agctaggcac cagctaaacc      2220
ctataattag tctcttatca acaccatccg ctcccccggg atcaatgagg agaatgaggg      2280
ggatgcgggg ctaaagaagc ctacataacc ctcatgccaa ctcccagttt acactcgtcg      2340
agccaacatc ctgactataa gctaacacag aatgcctcaa tcctgggaag aactggccgc      2400
tgataagcgc gcccgcctcg caaaaaccat ccctgatgaa tggaaagtcc agacgctgcc      2460
tgcggaagac agcgttattg atttcccaaa gaaatcgggc atcctttcag aggccgaact      2520
gaagatcaca gaggcctccg ctgcagatct tgtgtccaag ctggcggccg agagttgac       2580 ctcggtggaa gttacgctag cattctgtaa acgggcagca atcgcccagc agttagtagg      2640
gtcccctcta cctctcaggg agatgtaaca acgccacctt atgggactat caagctgacg      2700
ctggcttctg tgcagacaaa ctgcgcccac gagttcttcc ctgacgccgc tctcgcgcag      2760
gcaagggaac tcgatgaata ctacgcaaag cacaagagac ccgttggtcc actccatggc      2820
ctccccatct ctctcaaaga ccagcttcga gtcaaggtac accgttgccc ctaagtcgtt      2880
agatgtccct ttttgtcagc taacatatgc caccagggct acgaaacatc aatgggctac      2940
atctcatggc taaacaagta cgacgaaggg gactcggttc tgacaaccat gctccgcaaa      3000
gccggtgccg tcttctacgt caagacctct gtcccgcaga ccctgatggt ctgcgagaca      3060
gtcaacaaca tcatcgggcg caccgtcaac ccacgcaaca gaactggtc gtgcggcggc       3120 agttctggtg gtgagggtgc gatcgttggg attcgtggtg gcgtcatcgg tgtaggaacg      3180
gatatcggtg gctcgattcg agtgccggcc gcgttcaact tcctgtacgg tctaaggccg      3240
agtcatgggc ggctgccgta tgcaaagatg gcgaacagca tggagggtca ggagacggtg      3300
cacagcgttg tcgggccgat tacgcactct gttgagggtg agtccttcgc ctcttccttc      3360
ttttcctgct ctataccagg cctccactgt cctcctttct tgcttttat actatatacg       3420 agaccggcag tcactgatga agtatgttag acctccgcct cttcaccaaa tccgtcctcg      3480
gtcaggagcc atggaaatac gactccaagg tcatccccat gccctggcgc cagtccgagt      3540
cggacattat tgcctccaag atcaagaacg gcgggctcaa tatcggctac tacaacttcg      3600
acggcaatgt ccttccacac cctcctatcc tgcgcggcgt ggaaaccacc gtcgccgcac      3660
tcgccaaagc cggtcacacc gtgacccgt ggacgccata caagcacgat ttcggccacg       3720
atctcatctc ccatatctac gcggctgacg gcagcgccga cgtaatgcgc gatatcagtg      3780
catccggcga gccggcgatt ccaaatatca aagacctact gaacccgaac atcaaagctg      3840
ttaacatgaa cgagctctgg gacacgcatc tccagaagtg gaattaccag atggagtacc      3900
```

-continued

```
ttgagaaatg gcgggaggct gaagaaaagg ccgggaagga actggacgcc atcatcgcgc    3960
cgattacgcc taccgctgcg gtacggcatg accagttccg gtactatggg tatgcctctg    4020
tgatcaacct gctggatttc acgagcgtgg ttgttccggt tacctttgcg gataagaaca    4080
tcgataagaa gaatgagagt ttcaaggcgg ttagtgagct tgatgccctc gtgcaggaag    4140
agtatgatcc ggaggcgtac catggggcac cggttgcagt gcaggttatc ggacggagac    4200
tcagtgaaga gaggacgttg gcgattgcag aggaagtggg gaagttgctg ggaaatgtgg    4260
tgactccata gctaataagt gtcagatagc aatttgcaca agaaatcaat accagcaact    4320
gtaaataagc gctgaagtga ccatgccatg ctacgaaaga gcagaaaaaa acctgccgta    4380
gaaccgaaga gatatgacac gcttccatct ctcaaaggaa gaatcccttc agggttgcgt    4440
ttccagtcta gacgcgtttc taaatatcac gacaacacat cctccttcat ctggagattc    4500
ccggtcgcct tccagatcct cccctaatc cttctgttcc tcatcatctg gatcatgcct     4560 gaatccccc gctggctcgt caaagtgggt cgtgaagaag aggctcgctt catccttggt      4620
cgtctccgtg gcaatgaggg cgaggacggc ctcaaggcgg aagcagagta caatgatatt    4680
gtcaacatcc acaagcttga agtagacacc gccaagcagc agagctactt ctccatgttc    4740
tttggcattg ggtctggaaa gctacacact ggccggcgcg tgcagctggt catctggctc    4800
cagatattgc aagagtggat cggtattgcg ggaatcacca tttacggccc tgagatcttt    4860
acgattgctg gcatcagcgc aaaggacaga ctctgggtta gcgggatcaa caatatcaca    4920
tacatggtac gtttagccaa cacctcctca cctcaaagat tccatcacac taacacggga    4980
gcagttcgcc acactgatct gcgtcttcac catcgatcgc ataggtcgcc gttggactct    5040
gtactgggga gctgtcggcc agggcatttg catgttcgtc gccggtggcc tcgctcgcgc    5100
aaccatcaat gcctcaggca agcaagcca gagccacatc ggcggcgctg caacattctt     5160
tgtgttcctc tacactgcca ttttcggcgc tacctggctg ctacctggct gacggttcct    5220
tggttgtatc cggccgagat tttccctctg caggttagag ccaagggaaa tgcctggggt    5280
gtcgttggct ggtccattgg caacggctgg tgtgtaagtg cactttttcat tctcctctcc    5340 cgtctgggct cttctggtct aatcttctct aggtgctcct gcttcctacg atcttcaagg    5400
cgctcaacga aaagacactc tacatttttg gcgccgtcaa cgccctgtcc atcctcgtcg    5460
tgtgggctct gtaccccgaa tcgaatcaac gaactctaga ggagatggac ctcgtctttg    5520
ctagcgacag catctgggcc tgggaggctg agcgtaattt tgccaagctc aaggctgaaa    5580
acccggatct tgttcagggc tcaacaaacc acggagttgt agatattgag caagttgccg    5640
agccaaagga gtaggttcgt cgacaagaac ttgacggtct ctttatacat aattttttcct   5700 actactcgca tcaaactatt tcggcacgtg gacacattgt ccgctggagc tgggcatgtg    5760
tttaaaccaa cctcgattac ctcgcatgc                                      5789
```

<210> SEQ ID NO 11
<211> LENGTH: 37
<212> TYPE: DNA
<213> ORGANISM: Artificial Sequence
<220> FEATURE:
<223> OTHER INFORMATION: Oligo DNA for PCR.

<400> SEQUENCE: 11

```
atgcatctta agggtgcgta tgatagaata aagcagg                               37
```

<210> SEQ ID NO 12
<211> LENGTH: 35

```
<212> TYPE: DNA
<213> ORGANISM: Artificial Sequence
<220> FEATURE:
<223> OTHER INFORMATION: Oligo DNA for PCR.

<400> SEQUENCE: 12
atgcggccgc cggttgtgat tgtccaagaa tcatc                          35

<210> SEQ ID NO 13
<211> LENGTH: 33
<212> TYPE: DNA
<213> ORGANISM: Artificial Sequence
<220> FEATURE:
<223> OTHER INFORMATION: Oligo DNA for PCR.

<400> SEQUENCE: 13
atacgcgttt ctaaatatca cgacaacaca tcc                            33

<210> SEQ ID NO 14
<211> LENGTH: 33
<212> TYPE: DNA
<213> ORGANISM: Artificial Sequence
<220> FEATURE:
<223> OTHER INFORMATION: Oligo DNA for PCR.

<400> SEQUENCE: 14
atgcatgcga ggtaatcgag gttggtttaa aca                            33
```

TRICHODERMA FILAMENTOUS FUNGUS MUTANT STRAIN AND METHOD OF PRODUCING PROTEIN

TECHNICAL FIELD

This disclosure relates to a mutant strain of a filamentous fungus of the genus *Trichoderma*, the mutant strain having an enhanced protein-producing ability, and to a protein production method using the mutant strain.

BACKGROUND

Filamentous fungi of the genus *Trichoderma* are known for having a high protein-producing ability, and studies have heretofore been made on protein production using the filamentous fungi. Filamentous fungi of the genus *Trichoderma* are used especially to produce a cellulase classified as a saccharifying enzyme among proteins using cellulose, lactose, cellobiose or the like as an inducer.

Genetic modifications are being investigated to further increase cellulase production amount, in particular to enhance the production amount of β-glucosidase, which accounts for a small proportion of the saccharifying enzymes. Such investigations include overexpression or deletion of a factor which controls cellulase production. Juliano P, Single nucleotide polymorphism analysis of a *Trichoderma reesei* hyper-cellulolytic mutant developed in Japan, Bioscience, Biotechnology, and Biochemistry, Volume 77, 2013, Issue 3, P534-543 describes that a filamentous fungus of the genus *Trichoderma* was modified by reducing the function of Cre1, which is a transcription factor repressing cellulase production among the factors controlling cellulase production, thereby acquiring a mutant strain of the filamentous fungus of the genus *Trichoderma* having a high cellulase-producing ability.

Meanwhile, it is known that genetic modifications result in a decrease in cellulase production amount. Porciuncul Jde, Identification of Major Facilitator Transporters Involved in Cellulase Production during Lactose Culture of *Trichoderma reesei* PC-3-7, Biosci Biotechnol Biochem. 77, 1014-1022 (2013) describes that when *Trichoderma reesei* in which a sugar transporter thereof has been deleted is used together with lactose or cellulose as an inducer, cellulase production amount decreased.

As described above, a protein-production-controlling transcription factor in a filamentous fungus of the genus *Trichoderma* has been identified, but this is considered to be merely a part of the control mechanism. Thus, it could be helpful to acquire a mutant strain of a filamentous fungus of the genus *Trichoderma* having an enhanced protein-producing ability by making a search for a novel mechanism controlling protein production of the filamentous fungus of the genus *Trichoderma*, and to provide a protein production method using the mutant strain of the filamentous fungus of the genus *Trichoderma*.

SUMMARY

We believe that if a gene of a filamentous fungus of the genus *Trichoderma* which, when modified, can bring about an increase in protein production can be specified, then the amount of proteins that can be produced by the filamentous fungus of the genus *Trichoderma* can be further increased. We thus discovered that improvements in protein production property and β-glucosidase production property can be attained by cultivating a mutant strain of a filamentous fungus of the genus *Trichoderma*, the mutant strain having been reduced, by a genetic modification, in the function of a polypeptide consisting of the amino acid sequence represented by SEQ ID NO: 2.

We thus provide (1) to (6):

(1) A mutant strain of a filamentous fungus of the genus *Trichoderma*, having a reduced function of a polypeptide consisting of the amino acid sequence represented by SEQ ID NO: 2.

(2) The mutant strain of a filamentous fungus of the genus *Trichoderma* according to (1), in which at least 413th and succeeding amino acid residues from the N-terminal side in the amino acid sequence represented by SEQ ID NO: 2 is deleted.

(3) A method of producing a protein, the method including a step of cultivating the mutant strain of a filamentous fungus of the genus *Trichoderma* according to (1) or (2).

(4) A method of producing a cellulase, the method including a step of cultivating the mutant strain of a filamentous fungus of the genus *Trichoderma* according to (1) or (2).

(5) The method of producing a cellulase according to (4), the method including a step of cultivating the mutant strain of a filamentous fungus of the genus *Trichoderma* according to (1) or (2) in a culture medium including one or more kinds of inducers selected from the group consisting of lactose, cellulose, and xylan.

(6) A method of producing a sugar from a cellulose-containing biomass, the method including:

step a of producing a cellulase by cultivating a *Trichoderma reesei* mutant strain having a reduced function of a polypeptide consisting of the amino acid sequence represented by SEQ ID NO: 2; and step b of saccharifying the biomass by using the cellulase obtained in the step a.

The mutant strain of a filamentous fungus of the genus *Trichoderma* which has been reduced in the function of a polypeptide consisting of the amino acid sequence represented by SEQ ID NO: 2 has improved protein-producing ability as compared with the filamentous fungus of the genus *Trichoderma* in which the function of the polypeptide has not been reduced. Furthermore, especially when the produced protein is cellulases, an unexpected effect that the cellulases have various improved specific activities is also obtained.

DETAILED DESCRIPTION

A mutation is introduced into a parent strain of a filamentous fungus of the genus *Trichoderma*, which is a microorganism originally having an excellent protein-producing ability, to thereby further enhance the protein-producing ability. Consequently, the parent strain of a filamentous fungus of the genus *Trichoderma* is not limited to wild strains, and mutant strains of a filamentous fungus of the genus *Trichoderma* that have been improved to have an increased protein-producing ability can also be favorably used as the parent strain. For example, a mutant strain having an improved protein production property by performing a mutation treatment with a mutagen, UV irradiation or the like can be utilized as the parent strain of a mutant strain of a filamentous fungus of the genus *Trichoderma*. Specific examples of mutant strains usable as the parent strain include: *Trichoderma parareesei* (ATCC MYA-4777), which is an ancestor to *Trichoderma reesei*; QM6a strain (NBRC31326), QM9123 strain (ATCC24449), QM9414 strain (NBRC31329), PC-3-7 strain (ATCC66589). QM9123 strain (NBRC31327), RutC-30 strain (ATCC56765), CL-847 strain (Enzyme, Microbiol. Technol. 10, 341-346 (1988)), MCG77 strain (Biotechnol. Bioeng. Symp. 8, 89 (1978)), and MCG80 strain (Biotechnol. Bioeng. 12, 451-459 (1982)), which are known mutant strains derived from *Trichoderma reesei*; and strains derived from these. QM6a strain, QM9414 strain, and QM9123 strain are available from NBRC (NITE Biological Resource Center), and PC-3-7 strain and RutC-30 strain are available from ATCC (American Type Culture Collection).

The polypeptide consisting of an amino acid sequence represented by SEQ ID NO: 2 is a polypeptide possessed by filamentous fungi of the genus *Trichoderma*, and in the National Center for Biotechnology Information, this polypeptide is registered also as a predicted protein (EGR44419) that *Trichoderma reesei* QM6a strain has. The polypeptide consisting of the amino acid sequence represented by SEQ ID NO: 2 is a polypeptide whose function is not known, but Conserved Domain Architecture Retrieval Tool of National Center for Biotechnology Information discloses that the 26th to 499th amino acid residues from the N-terminal side have a sugar (and other) transporter domain. The polypeptide consisting of the amino acid sequence represented by SEQ ID NO: 2 participates at least in sugar transportation between the inside and the outside of the fungus bodies. The wording "reduced in the function of the polypeptide consisting of the amino acid sequence represented by SEQ ID NO: 2" means that a gene encoding EGR44419 has a mutation.

A decrease in the function of the polypeptide consisting of the amino acid sequence represented by SEQ ID NO: 2 indicates a state in which a base sequence encoding the amino acid sequence represented by SEQ ID NO: 2 has undergone a mutation, resulting in a decrease in or the elimination of the function of the polypeptide. Furthermore, also included in decreases in the function of the polypeptide consisting of the amino acid sequence represented by SEQ ID NO: 2 is when a base sequence other than a base sequence encoding the amino acid sequence represented by SEQ ID NO: 2 has undergone a mutation and this has resulted in a decrease in or the elimination of the expression of the polypeptide consisting of the amino acid sequence represented by SEQ ID NO: 2. A mutation of a base sequence is caused by substitution, deletion, insertion, or duplication of a base.

Specific examples of the gene encoding the polypeptide consisting of the amino acid sequence represented by SEQ ID NO: 2 include the base sequence represented by SEQ ID NO: 1.

Examples of methods of reducing the function of the polypeptide consisting of the amino acid sequence represented by SEQ ID NO: 2 include a method of introducing a mutation that causes a total deletion of a sugar (and other) transporter domain, a partial deletion of a sugar (and other) transporter domain, a change in the conformation of a sugar (and other) transporter domain, or a total deletion of the polypeptide consisting of the amino acid sequence represented by SEQ ID NO: 2. It is possible to reduce the function of the polypeptide consisting of the amino acid sequence represented by SEQ ID NO: 2, also by introducing a mutation that causes a decrease in or the elimination of the expression of the polypeptide.

The wording "deletion of a sugar (and other) transporter domain" means a total or partial loss of the domain, a change of the whole or some of the domain into different amino acid(s), or a combination of them. More specifically, that wording means that the sequence identity to the amino acid sequence of the sugar (and other) transporter domain becomes 80% or less, preferably 50% or less, more preferably 20% or less, more preferably 10% or less, more preferably 5% or less, more preferably 3% or less, more preferably 1% or less, and most preferably 0%.

Specific examples of when the function of a polypeptide consisting of the amino acid sequence represented by SEQ ID NO: 2 is reduced by a mutation such as deletion, substitution, or addition, that has occurred in the amino acid sequence located in a sugar (and other) transporter domain include a frame shift mutation in the base sequence represented by SEQ ID NO: 1 in which 11 bases have been inserted into the 1,415th position. It is presumed that the mutation causes the translation to end at the 419th position in the amino acid sequence represented by SEQ ID NO: 2 and this has shortened the amino acid sequence constituting the sugar (and other) transporter domain, resulting in a decrease in the original function.

The total deletion of a sugar (and other) transporter domain, the partial deletion of a sugar (and other) transporter domain, and the total deletion of a polypeptide consisting of the amino acid sequence represented by SEQ ID NO: 2 are attained by causing a gene sequence encoding the polypeptide consisting of the amino acid sequence represented by SEQ ID NO: 2 to undergo a frame shift or stop codon mutation due to base deletion, insertion, substitution or the like.

The decrease or elimination of the expression of a polypeptide consisting of the amino acid sequence represented by SEQ ID NO: 2 is attained by causing a mutation to the promoter or terminator region of the gene encoding the amino acid sequence represented by SEQ ID NO: 2. In general, the promoter and terminator regions correspond to a region of hundreds of bases in length before and after the gene participating in transcription. Specific examples of the base sequence containing a promoter and a terminator that participate in transcription of the polypeptide consisting of the amino acid sequence represented by SEQ ID NO: 2 include the base sequence represented by SEQ ID NO: 7.

To introduce such genetic mutations, use can be made of existing genetic mutation methods such as a mutation treatment with a known mutagen or with UV irradiation or the like, gene recombination such as homologous recombination using a selection marker, and a mutation by a transposon.

The mutant strain of a filamentous fungus of the genus *Trichoderma* has an enhanced protein-producing ability as compared with the filamentous fungus of the genus *Trichoderma* in which the function of the polypeptide consisting of the amino acid sequence represented by SEQ ID NO: 2 has not been reduced. When the mutant strain of a filamentous fungus of the genus *Trichoderma* is cultivated, an increased protein concentration is obtained as compared with a culture solution of the filamentous fungus of the genus *Trichoderma* in which the function of the polypeptide consisting of the amino acid sequence represented by SEQ ID NO: 2 has not been reduced. Furthermore, when the protein is an enzyme, the enzyme has increased specific activity. The protein concentration increase rate or enzyme specific activity increase rate is not particularly limited as long as the concentration or the specific activity has increased, but the increase rate is preferably 20% or more.

Besides having been reduced in the function of the polypeptide consisting of the amino acid sequence represented by SEQ ID NO: 2, the mutant strain of a filamentous fungus of the genus *Trichoderma* may have a gene mutation that brings about an improvement in protein production amount. Specific examples thereof include a gene mutation which reduces the function of a polypeptide represented by SEQ ID NO: 8. The polypeptide consisting of an amino acid sequence represented by SEQ ID NO: 8 is a polypeptide possessed by *Trichoderma reesei*, and in the National Center for Biotechnology Information, this polypeptide is registered as predicted protein EGR50654 that *Trichoderma reesei* QM6a strain has. The polypeptide consisting of the amino acid sequence represented by SEQ ID NO: 8 is a polypeptide whose function is not known, but Conserved Domain Architecture Retrieval Tool of National Center for Biotechnology Information discloses that the 95th to 277th amino acid residues from the N-terminal side have "Middle domain of eukaryotic initiation factor 4G domain" (hereinafter referred to as "MIF4G domain") and that the 380th to 485th amino acid residues from the N-terminal side have MA-3 domain. The two domains, MIF4G and MA-3, are known as having the function of binding to DNAs or RNAs (Biochem. 44, 12265-12272 (2005); Mol. Cell. Biol. 1, 147-156 (2007)). It is assumed from those disclosures that the polypeptide consisting of the amino acid sequence represented by SEQ ID NO: 8 at least has the function of binding to a DNA and/or an RNA.

Specific examples of genes encoding the polypeptide consisting of the amino acid sequence represented by SEQ ID NO: 8 include the base sequence represented by SEQ ID NO: 9. Examples of the gene mutation which reduces the function of EGR50654 include a total deletion of the MIF4G domain and/or MA-3 domain possessed by EGR50654, a partial deletion of the MIF4G domain and/or MA-3 domain, and a gene mutation which changes the configuration relationship between the MIF4G domain and the MA-3 domain. Furthermore, the function of the polypeptide consisting of the amino acid sequence represented by SEQ ID NO: 8 can be reduced also by introducing a mutation which decreases or eliminates the expression of the polypeptide. Specific examples of the deletion of the function of the polypeptide consisting of the amino acid sequence represented by SEQ ID NO: 8 include a mutation in the base sequence represented by SEQ ID NO: 9 which deletes any of the 1,039th to 1,044th bases.

We further provide a protein production method including a step of culturing the mutant strain of a filamentous fungus of the genus *Trichoderma*, the mutant strain having been reduced in a function of a polypeptide consisting of the amino acid sequence represented by SEQ ID NO: 2.

The protein to be produced is not particularly limited, but proteins to be secreted from the fungus body can be efficiently produced. Enzymes are preferred among these. More preferred are saccharifying enzymes such as cellulases, amylases, invertases, chitinases, and pectinases. Still more preferred are cellulases.

Cellulases that can be produced include various hydrolases, which include enzymes having a decomposition activity against xylan, cellulose, and hemicellulose. Specific examples thereof include cellobiohydrolase (EC 3.2.1.91), which produces cellobiose by hydrolyzing cellulose chains, endoglucanase (EC 3.2.1.4), which hydrolyzes cellulose chains from central portions thereof, β-glucosidase (EC 3.2.1.21), which hydrolyzes cellooligosaccharide and cellobiose, xylanase (EC 3.2.1.8), which is characterized by acting on hemicellulose and, in particular, on xylan, and β-xylosidase (EC 3.2.1.37), which hydrolyzes xylooligosaccharide. As stated above, whether the mutant strain of a filamentous fungus of the genus *Trichoderma* has an enhanced protein-producing activity is ascertained by ascertaining an improvement in cellulase specific activity by ascertaining that the specific activity of any of those hydrolases has improved. The produced cellulases have an improved activity of, in particular, β-glucosidase among those enzymes.

The β-glucosidase specific activity is determined by the following method. First, a 10 μL of an enzyme dilution is added to 90 μL of 50 mM acetate buffer containing 1 mM p-nitrophenyl-β-glucopyranoside (produced by Sigma-Aldrich Japan), and the mixture is allowed to react at 30° C. for 10 minutes. Then, 10 μL of 2 M sodium carbonate is added and mixed well to stop the reaction, and the increase in absorbance at 405 nm is measured. Finally, release of 1 μmol of p-nitrophenol per minute is defined as 1 U of activity, and the specific activity is calculated by dividing it by the protein amount.

The β-xylosidase specific activity is determined by the following method. First, a 10 μL of an enzyme dilution is added to 90 μL of 50 mM acetate buffer containing 1 mM p-nitrophenyl-β-xylopyranoside (produced by Sigma-Aldrich Japan), and the mixture is allowed to react at 30° C. for 30 minutes. Then, 10 μL of 2 M sodium carbonate is added and mixed well to stop the reaction, and the increase in absorbance at 405 nm is measured. Finally, release of 1 μmol of p-nitrophenol per minute is defined as 1 U of activity and, thus, the specific activity is calculated.

The cellobiohydrolase specific activity is determined by the following method. First, a 10 μL of an enzyme dilution is added to 90 μL of 50 mM acetate buffer containing 1 mM p-nitrophenyl-β-lactopyranoside (produced by Sigma-Aldrich Japan), and the mixture is allowed to react at 30° C. for 60 minutes. Then, 10 μL of 2 M sodium carbonate is added and mixed well to stop the reaction, and the increase in absorbance at 405 nm is measured. Finally, release of 1 μmol of p-nitrophenol per minute is defined as 1 U of activity, and the specific activity is calculated by dividing it by the protein amount.

The culture medium composition in the cultivating step is not particularly limited as long as it is a culture medium composition where *Trichoderma reesei* can produce a protein, and a known culture medium composition for microbe of the genus *Trichoderma* can be employed. As a nitrogen source, use can be made, for example, of polypeptone, bouillon, CSL, or soybean cake. An inducer for protein production may be added to the culture medium.

In producing cellulases by our methods, the mutant strain can be cultivated in a culture medium containing one or more inducers selected from the group consisting of lactose, cellulose, and xylan. To introduce cellulose or xylan, biomass containing cellulose or xylan may be added as an inducer. Specific examples of the biomass containing cellulose or xylan include not only plants such as seed plant, pteridophyte, bryophyte, algae, and water plant, but also waste building materials. The seed plants are classified into gymnosperms and angiosperms, and both can be used favorably. The angiosperms are further classified into monocotyledons and dicotyledons. Specific examples of the monocotyledons used preferably include bagasse, switchgrass, napier grass, erianthus, corn stover, corncob, rice straw, and wheat straw, and specific examples of the dicotyledons used preferably include beet pulp, eucalyptus, oak, and white birch.

As for the biomass containing cellulose or xylan, a pretreated product may be used. The pretreatment method is not particularly limited, but, for example, known methods such as acid treatment, sulfuric acid treatment, dilute sulfuric acid treatment, alkali treatment, hydrothermal treatment, subcritical treatment, fine grinding treatment, and steaming treatment can be used. Pulp may be used as the pretreated biomass containing cellulose or xylan.

Identification of Major Facilitator Transporters Involved in Cellulase Production during Lactose Culture of *Trichoderma reesei* PC-3-7 describes that when a mutant strain obtained by deleting a sugar transporter from *Trichoderma reesei* is cultivated, use of lactose as an inducer results in a decrease in cellulase production amount. However, when the mutant strain of a filamentous fungus of the genus *Trichoderma* is cultivated using lactose as an inducer, not only an improvement in protein production amount is attained but also various cellulase specific activities are improved.

Methods of cultivating the mutant of a filamentous fungus of the genus *Trichoderma* are not particularly limited, and the mutant can be cultivated, for example, by liquid culture using a centrifuge tube, a flask, a jar fermenter, a tank or the like or solid culture using a plate or the like. *Trichoderma reesei* is preferably cultivated under aerobic conditions, and among these culture methods, submerged culture of performing the culture by using a jar fermenter or while aerating and stirring in a tank is preferred. The aeration rate is preferably approximately 0.1-2.0 vvm, more preferably 0.3-1.5 vvm, particularly preferably 0.5-1.0 vvm. The culture temperature is preferably approximately 25-35° C., more preferably 25-31° C. The pH condition during culture is preferably pH 3.0 to 7.0, more preferably pH 4.0 to 6.0. As for the culture period, the culture is performed under conditions allowing for protein production until a recoverable amount of proteins are accumulated. Usually, the culture period is approximately 24-240 hours, more preferably 36-192 hours.

Methods of recovering a protein contained in the culture solution where the mutant of a filamentous fungus of the genus *Trichoderma* has been cultivated are not particularly limited, but the protein can be recovered by removing the fungus bodies of the filamentous fungus of the genus *Trichoderma* from the culture solution. Examples of methods of removing the fungus bodies include centrifugation, membrane separation, and filter press.

Furthermore, when the culture solution in which the mutant of the filamentous fungus of the genus *Trichoderma* has been cultivated is used as a protein solution without removing the fungus bodies therefrom, the culture solution is preferably treated so that the fungus bodies of the filamentous fungus of the genus *Trichoderma* cannot grow therein. Examples of treatment methods of preventing the fungus bodies from growing include heat treatment, chemical treatment, acid/alkali treatment, and UV treatment.

When the protein is an enzyme, the culture solution from which the fungus bodies have been removed or which has been treated so that the fungus body cannot grow as stated above, can be used directly as an enzyme solution.

The cellulases obtained by cultivating the mutant strain of a filamentous fungus of the genus *Trichoderma* in which the function of a polypeptide consisting of the amino acid sequence represented by SEQ ID NO: 2 has been reduced are high in various cellulase specific activities, in particular in the specific activity of β-glucosidase compared to cellulases obtained by cultivating the filamentous fungus of the genus *Trichoderma* in which the function of the polypeptide has not been reduced. Consequently, the cellulases can efficiently decompose cellulose-containing biomass to give a saccharified solution having a high glucose concentration, making it possible to obtain a larger quantity of sugar. Methods of saccharifying the cellulose-containing biomass to produce sugar are not particularly limited. The saccharification reaction may be performed in a batchwise method or a continuous method.

Conditions for the saccharification reaction are not particularly limited. The saccharification reaction temperature is preferably 25-60° C., more preferably 30-55° C. The saccharification reaction time is preferably 2-200 hours. The pH in the saccharification reaction is preferably 3.0-7.0, more preferably 4.0-6.0. In cellulases derived from the genus *Trichoderma*, the best pH for the reaction is 5.0. Furthermore, since the pH changes during the hydrolysis, it is preferred to add a buffer to the reaction solution or to conduct the reaction while keeping the pH constant by using an acid or an alkali.

The enzyme composition thus used can be separated and recovered from the saccharified solution obtained by saccharifying cellulose-containing biomass. Methods of separating and recovering the enzyme composition are not particularly limited. Use can be made of a method in which the saccharified solution is filtered with an ultrafiltration membrane or the like to recover the enzyme composition on the non-permeation side. According to need, a step of removing solid matter from the saccharified solution may be conducted before the filtration. The recovered cellulases can again be used for a saccharification reaction.

EXAMPLES

Our strains and methods are described specifically below by referring to Examples.

Reference Example 1, Method of Measuring Protein Concentration

A reagent to measure protein concentration (Quick Start Bradford protein assay, produced by Bio-Rad Laboratories, Inc.) was used. 5 µL of a diluted filamentous fungus culture solution was added to 250 µL of the protein concentration measurement reagent returned to room temperature. After leaving the mixture to stand at room temperature for 5 minutes, the absorbance at 595 nm was measured using a microplate reader. Using BSA as a standard, the protein concentration was calculated based on the calibration curve.

Reference Example 2, Method of Measuring Specific Activity of Cellulases Method of Measuring β-Glucosidase Specific Activity 10 µL of an enzyme dilution was added to 90 µL of 50 mM acetate buffer containing 1 mM p-nitrophenyl-β-glucopyranoside (produced by Sigma-Aldrich Japan), and the mixture was allowed to react at 30° C. for 10 minutes. Then, 10 µL of 2 M sodium carbonate was added and mixed well to stop the reaction, and the increase in absorbance at 405 nm was measured. Release of 1 µmol of p-nitrophenol per minute was defined as 1 U of activity, and the specific activity was calculated by dividing it by the protein amount.

Method of Measuring β-Xylosidase Specific Activity

10 µL of an enzyme dilution was added to 90 µL of 50 mM acetate buffer containing 1 mM p-nitrophenyl-β-xylopyranoside (produced by Sigma-Aldrich Japan), and the mixture was allowed to react at 30° C. for 30 minutes. Then, 10 µL of 2 M sodium carbonate was added and mixed well to stop the reaction, and the increase in absorbance at 405 nm was measured. Release of 1 µmol of p-nitrophenol per minute was defined as 1 U of activity, and the specific activity was calculated by dividing it by the protein amount.

Method of Measuring Cellobiohydrolase Specific Activity

10 μL of an enzyme dilution was added to 90 μL of 50 mM acetate buffer containing 1 mM p-nitrophenyl-β-lactopyranoside (produced by Sigma-Aldrich Japan), and the mixture was allowed to react at 30° C. for 60 minutes. Then, 10 μL of 2 M sodium carbonate was added and mixed well to stop the reaction, and the increase in absorbance at 405 nm was measured. Release of 1 μmol of p-nitrophenol per minute was defined as 1 U of activity, and the specific activity was calculated by dividing it by the protein amount.

Reference Example 3, Saccharification Test of Cellulose-Containing Biomass

As biomass to be saccharified, use was made of either wood-derived powdered cellulose Arbocel (registered trademark) B800 (produced by J. Rettenmaier & Sohne) or bagasse powdered into an average particle diameter of 100 μm. As an enzyme solution, use was made of a filtrate obtained by collecting a 1-mL portion of a culture solution of *Trichoderma reesei* or *Trichoderma reesei* mutant strain, centrifuging the collected culture solution, recovering a supernatant from which the fungus bodies had been removed, and filtrating the supernatant through a 0.22 μm filter. The wood-derived powdered cellulose Arbocel (registered trademark) B800 (produced by J. Rettenmaier & Sohne) is hereinafter often referred to as "Arbocel B800."
Saccharification Reaction A saccharification reaction was conducted in the following manner. Into a 2-mL tube were introduced Arbocel (registered trademark) B800 or bagasse powdered into an average particle diameter of 100 μm and a sodium acetate buffer (pH 5.2) to result in a final concentration of 0.1 M. Pure water was added in such an amount as to result in a solid concentration at the time of reaction initiation of 8% by weight in using the Arbocel (registered trademark) B800 or of 10% by weight in using the bagasse. The enzyme solution was further added to initiate the reaction under the reaction conditions of 50° C. using a heat block rotator. A sample obtained after the saccharification reaction had been conducted for 24 hours was centrifuged for 10 minutes under the conditions of 10,000×g and the supernatant was taken out. The saccharification reaction was terminated by adding 1 N sodium hydroxide aqueous solution to the supernatant in an amount of one-tenth the volume of the supernatant. The sugar concentration in the saccharified solution after the termination of the reaction was determined by subjecting the saccharified solution to sugar analysis by the UPLC shown below. As for the enzyme solution to be used in the saccharification reaction, the addition amount thereof was calculated from the protein concentration of the culture solution and the specific activity to be suitable for the conditions employed in each of the Examples and Comparative Examples.
Determination of Sugar Concentrations The saccharified solution was quantitatively analyzed for glucose, xylose, and cellobiose under the following conditions using ACQUITY (registered trademark) UPLC System (Waters).

The quantitative analysis was performed on the basis of calibration curves prepared with standard samples of glucose, xylose, and cellobiose. Cellobiose concentrations lower than 1 g/L were regarded as below the detection limit.

Column: AQUITY (registered trademark) UPLC BEH Amide 1.7 μm 2.1×100 mm Column

Separation method: HILIC

Mobile phase: mobile phase A: 80% acetonitrile, 0.2% TEA aqueous solution, and mobile phase B: 30% acetonitrile, 0.2% TEA aqueous solution, in accordance with the following gradient. The gradient was a linear gradient reaching the mixing ratio corresponding to the time below.

Initiation condition: (A 99.90%, B 0.10%), 2 minutes after initiation: (A 96.70%, B 3.30%), 3.5 minutes after initiation: (A 95.00%, B 5.00%), 3.55 minutes after initiation: (A 99.90%, B 0.10%), 6 minutes after initiation: (A 99.90%, B 0.10%)

Detection method: ELSD (evaporative light scattering detector)

Flow rate: 0.3 mL/min

Temperature: 55° C.

Example 1

Preparation of *Trichoderma reesei* QM9414 Mutant Strain I Reduced in the Function of Polypeptide Consisting of the Amino Acid Sequence Represented by SEQ ID NO: 2:

A *Trichoderma reesei* mutant strain reduced in the function of the polypeptide consisting of the amino acid sequence represented by SEQ ID NO: 2 was prepared by preparing a DNA fragment consisting of the gene sequence represented by SEQ ID NO: 3 as a DNA fragment containing a gene encoding the polypeptide consisting of the amino acid sequence represented by SEQ ID NO: 2 in which the function of the polypeptide consisting of the amino acid sequence represented by SEQ ID NO: 2 had been reduced, and then transforming *Trichoderma reesei* QM9414 strain with the DNA fragment. By this method, a *Trichoderma reesei* mutant strain is obtained in which 11 bases have been inserted into the 1,415th position in SEQ ID NO: 1 to have a polypeptide in which the translation ends at the 419th position in SEQ ID NO: 2. Acetamide and acetamidase (AmdS) gene (amdS) capable of decomposing acetamide were used as selection markers for introducing the DNA fragment. To allow the DNA fragment consisting of the base sequence represented by SEQ ID NO: 3 to be introduced upstream and downstream of the amdS-containing DNA sequence, a plasmid for mutation introduction was prepared to add a portion homologous to the gene sequence of the *Trichoderma reesei* QM9414 strain.

Specifically, a DNA fragment obtained by treating a synthesized DNA fragment shown by SEQ ID NO: 4 with restriction enzymes AflII and NotI was used as the upstream DNA fragment. In addition, PCR was conducted using genomic DNA extracted in a usual manner from the *Trichoderma reesei* QM9414 strain and oligo DNAs represented by SEQ ID NOs: 5 and 6, and a DNA fragment obtained by treating the resulting amplified fragment with restriction enzymes MluI and SwaI was used as the downstream DNA fragment. The upstream and downstream DNA fragments were introduced into an amdS-inserted plasmid by using restriction enzymes AflII and NotI and restriction enzymes MluI and SwaI, respectively, to construct a plasmid for mutation introduction. The plasmid for mutation introduction was then treated with restriction enzymes PacI and AscI, and the *Trichoderma reesei* QM9414 strain (NBRC #31329) was transformed with the obtained DNA fragment shown by SEQ ID NO: 3. The manipulations involving the molecular biological technique were performed as described in Molecular cloning, laboratory manual, 1st, 2nd, 3rd (1989). In addition, the transformation was carried out using a standard technique, i.e., a protoplast PEG method, and specifically, was performed as described in Gene, 61, 165-

176 (1987). The obtained *Trichoderma reesei* mutant strain was used as QM9414 mutant strain I in the following experiments.

Example 2

Protein Production Test Using QM9414 Mutant Strain I: Flask Cultivation

After spores of QM9414 mutant strain I prepared in Example 1 were diluted with physiological saline to be $1.0 \times 10^7$/mL, 0.1 mL of the diluted spore solution was inoculated into 10 mL of a flask medium shown in Table 1 or 2 which had been placed in a 50 mL baffled flask, and was incubated on a shaker under the conditions of 28° C. and 120 rpm for 120 hours. The protein concentration in the culture solution was determined by the method described in Reference Example 1, and the various cellulase specific activities were determined by the methods described in Reference Example 2. The results obtained after the cultivation in the culture medium shown in Table 1 are given in Table 3, and the results obtained after the cultivation in the culture medium shown in Table 2 are given in Table 4.

TABLE 1

| | |
|---|---|
| Arbocel B800 (produced by J. Rettenmaier & Sohne) | 20 g |
| 5× Mandel's solution* | 200 mL |
| 10× Ammonium tartrate solution** | 100 mL |
| Corn steep liquor | 50 g |
| Trace element solution*** | 1 mL |
| Tween 80 | 0.5 mL |
| PE-M | 1 mL |
| | (per 1 L) |

*The 5× Mandel's solution contains 7 g/L $(NH_4)_2SO_4$, 10 g/L $KH_2PO_4$, 2 g/L $CaCl_2 \cdot 2H_2O$, and 1.5 g/L $MgSO_4 \cdot 7H_2O$.
**The 10× Ammonium tartrate solution contains 92 g/L ammonium tartrate.
***The trace element solution contains 0.3 g/L $H_3BO_3$, 1.3 g/L $(NH_4)_6Mo_7O_{24} \cdot 4H_2O$, 5 g/L $FeCl_3 \cdot 6H_2O$, 2 g/L $CuSO_4 \cdot 5H_2O$, 0.4 g/L $MnCl_2 \cdot 4H_2O$, and 10 g/L $ZnCl_2$.

TABLE 2

| | |
|---|---|
| Lactose | 20 g |
| 5× Mandel's solution* | 200 mL |
| 10× Ammonium tartrate solution** | 100 mL |
| Corn steep liquor | 50 g |
| Trace element solution*** | 1 mL |
| Tween 80 | 0.5 mL |
| PE-M | 1 mL |
| | (per 1 L) |

Collection of Culture Solution

After 120 hours from the start of cultivation, a 1-mL portion of the culture solution was collected. The collected culture solution was centrifuged under the conditions of 15,000×g and 4° C. for 10 minutes to obtain a supernatant. The supernatant was filtrated through a 0.22 μm filter, and the filtrate was used as a cellulase solution in the following experiments.

Determination of Protein Concentration and Various Cellulase Specific Activities The protein concentration in the culture solution at 120 hours from the start of cultivation was determined using the technique described in Reference Example 1, and subsequently, the specific activities of the cellulases were determined by the methods described in Reference Example 2. The results are shown in Tables 3 and 4.

Example 3

Preparation of *Trichoderma reesei* QM9414 Mutant Strain II Reduced in the Function of Polypeptide Consisting of the Amino Acid Sequence Represented by SEQ ID NO: 2:

A *Trichoderma reesei* mutant strain reduced in the function of the polypeptide consisting of the amino acid sequence represented by SEQ ID NO: 2 was prepared by producing a DNA fragment consisting of the gene sequence represented by SEQ ID NO: 10, and then transforming *Trichoderma reesei* QM9414 strain with the DNA fragment. By this method, amdS is inserted between the 435th and 436th bases in SEQ ID NO: 1, and a *Trichoderma reesei* mutant strain reduced in the function of SEQ ID NO: 2 is obtained. For allowing the DNA fragment consisting of the base sequence represented by SEQ ID NO: 10 to be introduced upstream and downstream of the amdS-containing DNA sequence, a plasmid for mutation introduction was prepared to add a portion homologous to the gene sequence of the *Trichoderma reesei* QM9414 strain.

Specifically, PCR was conducted using genomic DNA extracted in a usual manner from the *Trichoderma reesei* QM9414 strain and oligo DNAs represented by SEQ ID NOs: 11 and 12, and a DNA fragment obtained by treating the resulting amplified fragment with restriction enzymes AflII and NotI was used as the upstream fragment. In addition, PCR was conducted using genomic DNA and oligo DNAs represented by SEQ ID NOs: 13 and 14, and a DNA fragment obtained by treating the resulting amplified fragment with restriction enzymes MluI and SphI was used as the downstream DNA fragment. The upstream and downstream DNA fragments were introduced into an amdS-inserted plasmid by using restriction enzymes AflII and NotI and restriction enzymes MluI and SphI, respectively, to construct a plasmid for mutation introduction. The plasmid for mutation introduction was then treated with restriction enzymes AflII and SphI, and the *Trichoderma reesei* QM9414 strain was transformed with the obtained DNA shown by SEQ ID NO: 10 in the manner as described in Example 1. The obtained *Trichoderma reesei* mutant strain was used as QM9414 mutant strain II in the following experiments.

Example 4

Protein Production Test Using QM9414 Mutant Strain II:

Cultivation was performed by the same operations and conditions as in Example 2 except that QM9414 mutant strain II was used in place of QM9414 mutant strain I prepared in Example 1, and the protein concentration in the culture solution and the various cellulase specific activities were determined. The results are shown in Tables 3 and 4.

Comparative Example 1

Protein Production Test Using *Trichoderma reesei* QM9414 Strain

Cultivation was performed by the same conditions and operations as in Example 2 except that *Trichoderma reesei* QM9414 strain was used in place of QM9414 mutant strain I prepared in Example 1, and the protein concentration in the culture solution and the various cellulase specific activities were determined by the same methods as in Example 2. The results obtained after the cultivation in the culture medium shown in Table 1 are given in Table 3, and the results obtained after the cultivation in the culture medium shown in Table 2 are given in Table 4.

TABLE 3

| Cultivation with Arbocel B800 | Comparative Example 1 QM9414 Strain | Example 2 QM9414 Mutant Strain I | Example 4 QM9414 Mutant Strain II |
|---|---|---|---|
| Relative value of protein Concentration | 1 | 1.5 | 1.3 |
| Relative value of β-glucosidase specific activity | 1 | 1.9 | 1.7 |
| Relative value of β-xylosidase specific activity | 1 | 1.3 | 1.9 |
| Relative value of cellobiohydrolase specific activity | 1 | 1.3 | 1.1 |

TABLE 4

| Cultivation with lactose | Comparative Example 1 QM9414 Strain | Example 2 QM9414 Mutant Strain I | Example 4 QM9414 Mutant Strain II |
|---|---|---|---|
| Relative value of protein Concentration | 1 | 1.7 | 1.4 |
| Relative value of β-glucosidase specific activity | 1 | 4.3 | 1.6 |
| Relative value of β-xylosidase specific activity | 1 | 2.5 | 1.2 |
| Relative value of cellobiohydrolase specific activity | 1 | 3.5 | 1.1 |

The results of Example 2, Example 4, and Comparative Example 1 revealed the following regarding the cultivation in the medium shown in Table 1. When the protein concentration in the culture solution where the *Trichoderma reesei* QM9414 strain had been cultivated was assumed to be 1, the relative value of the protein concentration in the culture solution of QM9414 mutant strain I was 1.5 and the relative value of the protein concentration in the culture solution of QM9414 mutant strain II was 1.3. It can be seen from these results that when *Trichoderma reesei* reduced in the function of the polypeptide consisting of the amino acid sequence represented by SEQ ID NO: 2 is cultivated, the protein production amount can be increased compared to when the function of the polypeptide has not been reduced.

Furthermore, the culture solutions obtained in Example 2, Example 4, and Comparative Example 1 were examined for cellulase specific activity by the methods described in Reference Example 2. As a result, we found the following. When various cellulase specific activities in the culture solution where *Trichoderma reesei* QM9414 strain had been cultivated were assumed to be 1, the β-glucosidase specific activity was QM9414 mutant strain I: 1.9, and QM9414 mutant strain II: 1.7, the β-xylosidase specific activity was QM9414 mutant strain I: 1.3, and QM9414 mutant strain II: 1.9, and the cellobiohydrolase specific activity was QM9414 mutant strain I: 1.3, and QM9414 mutant strain II: 1.1. It was understood from these results that the cellulases obtained by cultivating the *Trichoderma reesei* mutant strains reduced in the function of the polypeptide represented by the amino acid sequence represented by SEQ ID NO: 2 not only attain improved protein production amounts but also bring about an unexpected effect that an improvement in various cellulase specific activities is attained compared to when the function of the polypeptide has not been reduced.

Meanwhile, with respect to the cultivation in the lactose-containing culture medium shown in Table 2, we found the following. When the protein concentration in the culture solution where the QM9414 strain had been cultivated was assumed to be 1, the relative value of the protein concentration in the culture solution of QM9414 mutant strain I was 1.7 and the relative value of the protein concentration in the culture solution of QM9414 mutant strain II was 1.4. It can be seen from these results that when *Trichoderma reesei* reduced in the function of the polypeptide consisting of the amino acid sequence represented by SEQ ID NO: 2 is cultivated, the protein production amount can be increased compared to when the function of the polypeptide has not been reduced.

Furthermore, the obtained culture solutions were examined for cellulase specific activity by the methods described in Reference Example 2. As a result, we found the following. When various cellulase specific activities in the culture solution where QM9414 strain had been cultivated were assumed to be 1, the β-glucosidase specific activity was QM9414 mutant strain 1:4.3, and QM9414 mutant strain II: 1.6, the β-xylosidase specific activity was QM9414 mutant strain 1:2.5, and QM9414 mutant strain 11:1.2, and the cellobiohydrolase specific activity was QM9414 mutant strain I: 3.5, and QM9414 mutant strain 11:1.1. It can be seen from these results that the cellulases obtained by cultivating the *Trichoderma reesei* mutant strains reduced in the function of the polypeptide represented by the amino acid sequence represented by SEQ ID NO: 2 not only attain improved protein production amounts but also bring about an unexpected effect that an improvement in various cellulase specific activities is attained compared to when the function of the polypeptide has not been reduced. These results revealed that the cultivation of QM9414 mutant strain I, which has been reduced in the function of the polypeptide consisting of the amino acid sequence represented by SEQ ID NO: 2, in the lactose-containing culture medium attains greater improvements in various cellulase specific activities than the cultivation thereof in the cellulose-containing culture medium.

Example 5

Saccharification Reaction Test Using Cellulases from QM9414 Mutant Strain I

Using a culture solution collected at 120 hours after initiation of the cultivation of QM9414 mutant strain I obtained in Example 2 in the culture medium shown in Table 1, a saccharification reaction test of cellulose-containing biomass was performed in accordance with the operation and conditions described in Table 5 and Reference Example 3. As the cellulose-containing biomass, use was made of Arbocel (registered trademark) B800 or powdered bagasse. The results thereof are shown in Table 6.

TABLE 5

| Arbocel B800 or powdered bagasse | 80 mg |
|---|---|
| 1M sodium acetate buffer (pH 5.2) | 100 μL |
| Enzyme addition amount | 0.06 mg (per 1 mL) |

TABLE 6

| | | Comparative Example QM9414 Strain | Example 5 QM9414 Mutant Strain I |
|---|---|---|---|
| Arbocel B800 | Glucose concentration (g/L) | 3.3 | 4.8 |
| | Xylose concentration (g/L) | 3.9 | 4.9 |

TABLE 6-continued

|  |  | Comparative Example QM9414 Strain | Example 5 QM9414 Mutant Strain I |
|---|---|---|---|
| Bagasse | Glucose concentration (g/L) | 1.4 | 1.7 |
|  | Xylose concentration (g/L) | 2.3 | 2.5 |

Example 6

Saccharification Reaction Test 1 Using Cellulases from QM9414 Mutant Strain II

A saccharification reaction test of cellulose-containing biomass was performed in accordance with the operation and conditions described in Reference Example 3 using a culture solution collected at 120 hours after initiation of the cultivation in the culture medium shown in Table 1, of the culture solutions of QM9414 mutant strain II obtained in Example 4. Reaction conditions for the saccharification reaction of Arbocel (registered trademark) B800 are shown in Table 7, and reaction conditions for the saccharification reaction of powdered bagasse are shown in Table 8. The results thereof are shown in Table 9.

TABLE 7

| Arbocel B800 | 100 mg |
| 1M sodium acetate buffer (pH 5.2) | 100 uL |
| Enzyme addition amount | 450 uL (per 1 mL) |

TABLE 8

| Powdered bagasse | 100 mg |
| 1M sodium acetate buffer (pH 5.2) | 100 uL |
| Enzyme addition amount | 400 uL (per 1 mL) |

TABLE 9

| Supernatant of culture medium from Arbocel B800 cultivation was used |  | Comparative Example QM9414 Strain | Example 6 QM9414 Mutant Strain II |
|---|---|---|---|
| Saccharification of Arbocel B800 | Glucose concentration (g/L) | 13.0 | 14.3 |
|  | Xylose concentration (g/L) | 8.5 | 9.1 |
| Saccharification of Bagasse | Glucose concentration (g/L) | 6.1 | 6.5 |
|  | Xylose concentration (g/L) | 4.1 | 4.1 |

Comparative Example 2

Saccharification Reaction Test 1 Using Cellulases from *Trichoderma reesei* QM9414 Strain A saccharification reaction test of cellulose-containing biomass was performed using the same operation and conditions as in Example 5 or 6, except that use was made of a culture solution collected at 120 hours after initiation of the cultivation in the culture medium shown in Table 1, of the culture solutions of *Trichoderma reesei* QM9414 strain obtained in Comparative Example 1. The results thereof are shown in Tables 6 and 9.

Example 7

Saccharification Reaction Test 2 Using Cellulases from QM9414 Mutant Strain II

A saccharification reaction test of cellulose-containing biomass was performed in accordance with the operation and conditions described in Table 6 and Reference Example 3 using a culture solution collected at 120 hours after initiation of the cultivation in the culture medium shown in Table 2, of culture solutions of QM9414 mutant strain II obtained in Example 4. Reaction conditions for the saccharification reaction of Arbocel (registered trademark) B800 are shown in Table 10, and reaction conditions for the saccharification reaction of powdered bagasse are shown in Table 11. The results thereof are shown in Table 12.

TABLE 10

| Arbocel B800 | 100 mg |
| 1M sodium acetate buffer (pH 5.2) | 100 uL |
| Enzyme addition amount | 350 uL (per 1 mL) |

TABLE 11

| Powdered bagasse | 100 mg |
| 1M sodium acetate buffer (pH 5.2) | 100 uL |
| Enzyme addition amount | 400 uL (per 1 mL) |

TABLE 12

| Supernatant of culture medium from lactose cultivation was used |  | Comparative Example QM9414 Strain | Example 6 QM9414 Mutant Strain II |
|---|---|---|---|
| Saccharification of Arbocel B800 | Glucose concentration (g/L) | 5.9 | 7.2 |
|  | Xylose concentration (g/L) | 3.4 | 4.5 |
| Saccharification of Bagasse | Glucose concentration (g/L) | 2.9 | 3.9 |
|  | Xylose concentration (g/L) | 2.5 | 3.0 |

Comparative Example 3

Saccharification Reaction Test 2 Using Cellulases from *Trichoderma reesei* QM9414 Strain A saccharification reaction test of cellulose-containing biomass was performed using the same operation and conditions as in Example 7, except that use was made of a culture solution collected at 120 hours after initiation of the cultivation in the culture medium shown in Table 2, of the culture solutions of *Trichoderma reesei* QM9414 strain obtained in Comparative Example 1. The results thereof are shown in Table 12.

CONCLUSIONS

The results of Example 5 and Comparative Example 2 revealed the following. With respect to the saccharification reaction of Arbocel (registered trademark) B800 with the culture solutions obtained by the cultivation in the culture medium shown in Table 1, use of the cellulases obtained from the *Trichoderma reesei* QM9414 strain resulted in a saccharified solution having a glucose concentration of 3.3 g/L, whereas use of the QM9414 mutant strain I resulted in a glucose concentration of 4.8 g/L. Furthermore, use of the QM9414 strain resulted in a xylose concentration in the saccharified solution of 3.9 g/L, whereas use of the QM9414 mutant strain I resulted in a xylose concentration of 4.9 g/L.

With respect to the saccharification reaction of the powdered bagasse, use of the QM9414 strain resulted in a free glucose content of 1.4 g/L, whereas use of the mutant strain I resulted in a free glucose content of 1.7 g/L. Use of the QM9414 strain resulted in a free xylose content of 2.3 g/L, whereas use of the mutant strain I resulted in a free xylose content of 2.5 g/L.

The results of Example 6 and Comparative Example 2 revealed the following. With respect to the saccharification reaction of Arbocel (registered trademark) B800 with the culture solutions obtained by the cultivation in the culture medium shown in Table 1, use of the QM9414 strain resulted in a free glucose content of 13 g/L, whereas use of the QM9414 mutant strain II resulted in a free glucose content of 14.3 g/L. Furthermore, use of the QM9414 strain resulted in a free xylose content of 8.5 g/L, whereas use of the mutant strain II resulted in a free xylose content of 9.1 g/L. With respect to the saccharification reaction of the powdered bagasse, use of the QM9414 strain resulted in a free glucose content of 6.1 g/L, whereas use of the mutant strain II resulted in a free glucose content of 6.5 g/L. Both the QM9414 strain and the mutant strain II gave a free xylose content of 4.1 g/L.

The results of Example 7 and Comparative Example 3 revealed the following. With respect to the saccharification reaction of Arbocel (registered trademark) B800 with the culture solutions obtained by the cultivation in the culture medium shown in Table 2, use of the QM9414 strain resulted in a glucose concentration of 5.9 g/L, whereas use of the mutant strain II resulted in a glucose concentration of 7.2 g/L. Furthermore, use of the QM9414 strain resulted in a xylose concentration of 3.4 g/L, whereas use of the mutant strain II resulted in a xylose concentration of 4.5 g/L. With respect to the saccharification reaction of the powdered bagasse, use of the QM9414 strain resulted in a glucose concentration of 2.9 g/L, whereas use of the mutant strain II resulted in a glucose concentration of 3.9 g/L. Use of the QM9414 strain resulted in a xylose concentration of 2.5 g/L, whereas use of the mutant strain II resulted in a xylose concentration of 3.0 g/L. It can be seen from these results that the cellulases produced by the mutant strains of a filamentous fungus of the genus *Trichoderma* which have been reduced in the function of the polypeptide consisting of the amino acid sequence represented by SEQ ID NO: 2 can produce a larger quantity of sugar than the cellulases produced by the QM9414 strain.

The invention claimed is:

1. A mutant strain of a filamentous fungus of the genus *Trichoderma reesei*, having a reduced expression of a polypeptide consisting of the amino acid sequence of SEQ ID NO: 2, wherein the mutant strain has improved production ability for cellulase compared to an unmodified *Trichoderma reesei* parent strain of the mutant strain.

2. A method of producing a protein, the method comprising a step of cultivating the mutant strain of a filamentous fungus of the genus *Trichoderma reesei* according to claim 1.

3. A method of producing a cellulase, the method comprising a step of cultivating the mutant strain of a filamentous fungus of the genus *Trichoderma reesei* according to claim 1.

4. The method of producing a cellulase according to claim 3, the method comprising a step of cultivating the mutant strain, in a culture medium comprising one or more kinds of inducers selected from the group consisting of lactose, cellulose, and xylan.

5. A method of producing a sugar from a cellulose-containing biomass, the method comprising:

step a of producing a cellulase by cultivating the *Trichoderma reesei* mutant strain of claim 1; and step b of saccharifying the biomass by using the cellulase obtained in the step a.

* * * * *